US008542916B2

(12) United States Patent
Tognoli et al.

(10) Patent No.: US 8,542,916 B2
(45) Date of Patent: Sep. 24, 2013

(54) SYSTEM AND METHOD FOR ANALYSIS OF SPATIO-TEMPORAL DATA

(75) Inventors: Emmanuelle Tognoli, Boca Raton, FL (US); J. A. Scott Kelso, Boynton Beach, FL (US)

(73) Assignee: Florida Atlantic University, Boca Raton, FL (US)

( * ) Notice: Subject to any disclaimer, the term of this patent is extended or adjusted under 35 U.S.C. 154(b) by 1044 days.

(21) Appl. No.: 12/500,187

(22) Filed: Jul. 9, 2009

(65) Prior Publication Data

US 2010/0098289 A1   Apr. 22, 2010

Related U.S. Application Data

(60) Provisional application No. 61/134,349, filed on Jul. 9, 2008.

(51) Int. Cl.
  *G06K 9/00*   (2006.01)
(52) U.S. Cl.
  USPC .......................................................... 382/164
(58) Field of Classification Search
  USPC .......................................................... 382/164
  See application file for complete search history.

(56) References Cited

U.S. PATENT DOCUMENTS

| | | | | |
|---|---|---|---|---|
| 5,282,474 A * | 2/1994 | Valdes Sosa et al. | ......... | 600/483 |
| 2002/0126891 A1 * | 9/2002 | Osberger | .................... | 382/165 |
| 2005/0002572 A1 * | 1/2005 | Saptharishi et al. | .......... | 382/224 |
| 2006/0072799 A1 * | 4/2006 | McLain | ....................... | 382/128 |
| 2006/0242146 A1 * | 10/2006 | Piacsek et al. | .................... | 707/7 |
| 2008/0062164 A1 * | 3/2008 | Bassi et al. | .................... | 345/214 |
| 2009/0016587 A1 * | 1/2009 | Strobel et al. | ................. | 382/130 |
| 2009/0124923 A1 * | 5/2009 | Sackellares et al. | ......... | 600/544 |
| 2009/0136102 A1 * | 5/2009 | Kimpe et al. | ................. | 382/128 |
| 2009/0137881 A1 * | 5/2009 | Ebert et al. | .................... | 600/300 |
| 2010/0066756 A1 * | 3/2010 | Yang | ............................ | 345/593 |

OTHER PUBLICATIONS

Emmanuelle Tognoli et al, The phi complex as a neuromarker of human social coordination. In: Proceedings of the National Academy of Sciences of the United States of America.

Emmanuelle Tognoli, J.A. Scott Kelso, Brain coordination dynamics: True and false faces of phase synchrony and metastability. Progress in Neurobiology, Jan. 2009, vol. 87.

Thomas Ebert. Andreas Keil, Imaging in the Fourth Dimension; News Views; Nature vol. 404, Mar. 2, 2000.

* cited by examiner

*Primary Examiner* — Jingge Wu
(74) *Attorney, Agent, or Firm* — Novak Druce Connolly Bove + Quigg LLP

(57) ABSTRACT

A system and method of analyzing at least one dataset having temporal and spatial content is provided. A method includes the steps of applying a colorimetric mapping to the dataset based on the spatial content (500), segmenting the dataset (618) into one of a plurality of patterns based on a spatio-temporal analysis of the dataset (604, 606), and analyzing characteristics of each of the plurality of patterns (612-622).

10 Claims, 17 Drawing Sheets

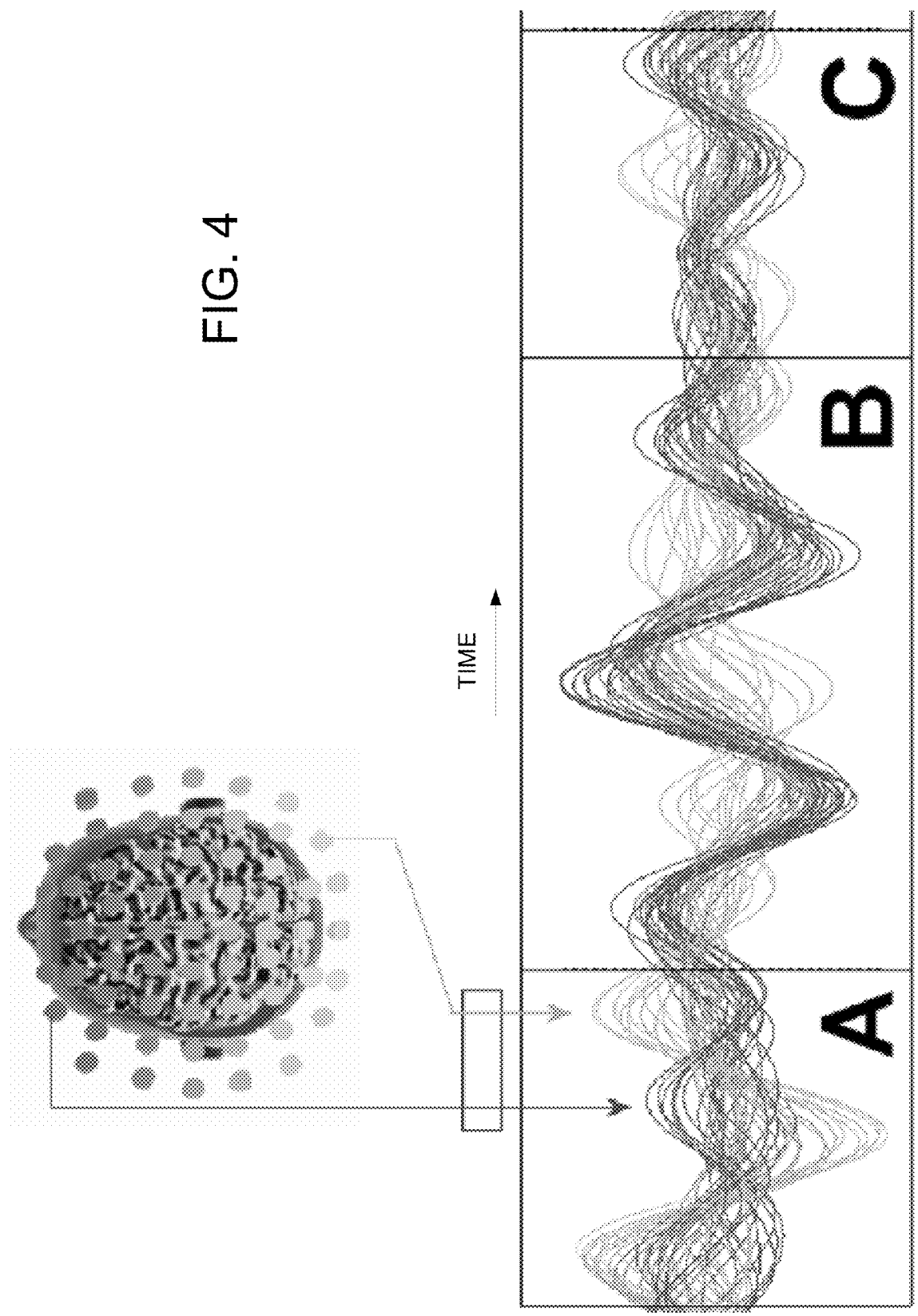

500

600

1500

1600

SYSTEM AND METHOD FOR ANALYSIS OF SPATIO-TEMPORAL DATA

CROSS REFERENCE TO RELATED APPLICATIONS

This application claims the benefit of Provisional Application Ser. No. 61/134,349 entitled "SYSTEM AND METHOD FOR ANALYSIS OF SPATIO-TEMPORAL DATA", filed Jul. 9, 2008, which is herein incorporated by reference in its entirety.

STATEMENT REGARDING FEDERALLY SPONSORED RESEARCH OR DEVELOPMENT

The invention was made with government support under awards MH042900 and MH080838 from the U.S. National Institute of Mental Health, award NS048229-04 from the U.S. National Institute of Neurological Disorders and Stroke, contracts N00014-05-1-0117 and N00014-09-1-0527 from the U.S. Office of Naval Research, and award BCS0826897 from the U.S. National Science Foundation.

FIELD OF THE INVENTION

The present invention relates to data analysis, and more specifically to systems and methods for analysis of spatio-temporal data.

BACKGROUND

Many systems in nature can be described in space and time. The temporal dynamics of a variable can be visualized as a 2-dimensional graph with time (t) on the abscissa and measurements of the variable (s) on the ordinate axis. This graph leaves no room for the representation of the spatial organization of the variable: that is, how values of the measurement change from place to place in the spatial domain of the system. Alternatively, measurements can be represented as a three-dimensional graph, with a set of coordinates expressing the spatial domain of the system (typically a 2-dimensional projection/reduction/representation of the original space (x, y, z)), and a luminance, intensity or color scale superimposed on this map to describe the values of the variable(s). This graph leaves no room to represent information about time; only a movie with a succession of maps would reveal how the variable changes over space and over time. Note that such a movie would not render instantaneous insight about the spatio-temporal patterning of the system because it relies on observers' memory of the previous frames, which is inherently fluctuant over time and other space; and because it depends on how/where attention is deployed during exposure to the succession of images (also fluctuant in space and in time).

In general, visualizing the fourth dimension of time using a static display (e.g., paper or an unanimated computer screen) in such a manner as to obtain a simultaneous and perceptually intuitive representation of the system is difficult due to the limits of the human perceptual system. For example, it is cumbersome to extract multi-variate information in such a manner that it can be 'grasped' and 'understood' in its complete form by human observers. In practice, massive analysis procedures are used to mine such data sets, but they never bring out the complete patterning of the system. The difficulty arises as soon as the dimensionality of the data set exceeds the dimensional constraints of the human visual system. As a result, observers of high dimensional spatio-temporal datasets are left with the burden of going back and forth between multiple partial views of the system's original variables (or its derived quantities) when working with static displays, or to employ movie animations to explore the system. However, such approaches still lack the ability to grasp all dimensions of the problem at once.

For example, the study of brain dynamics is an area which typically requires analysis of data in four dimensions. The brain is a complex system, formed by a multitude of functional units (brain areas) wired together via so-called long-range connections. At every moment, interconnected brain areas generate dynamical behaviors that must accommodate both their local (intrinsic) properties and the mutual influence they exert on each. This self-organized and non-stationary system has been shown to operate in non-equilibrium regimes. Dynamics is a chief aspect of brain function, and dynamical descriptions of the brain are irreducible to the description of time-aggregated quantities that are commonly employed to characterize this organ (topographical maps, evoked potentials, average spectra . . . ). However, conventional tools for studying brain dynamics typically provide only two- and three-dimensional representations of brain function. These representations only convey partial information about the spatio-temporal organization of the dataset and fail to integrate this information into a comprehensive, readily understandable picture.

SUMMARY

This Summary is provided to comply with 37 C.F.R. §1.73, presenting a summary of the invention to briefly indicate the nature and substance of the invention. It is submitted with the understanding that it will not be used to interpret or limit the scope or meaning of the claims.

Embodiments of the invention provide systems and method for analysis of spatio-temporal data. In a first embodiment, a method of analyzing at least one dataset having temporal and spatial content is provided. The method includes the steps of applying a colorimetric mapping to the dataset based on the spatial content, segmenting the dataset into one of a plurality of patterns based on a spatio-temporal analysis of the dataset, and analyzing characteristics of each of the plurality of patterns.

In a second embodiment of the invention, a system for analyzing spatio-temporal data is provided. The system includes a storage element for receiving at least one dataset having temporal and spatial content and a processing element. The processing element is configured for applying a colorimetric mapping to the dataset based on the spatial content, segmenting the dataset into one of a plurality of patterns based on a spatio-temporal analysis of the dataset, and analyzing each of the plurality of patterns based on the selected characteristics.

In a third embodiment of the invention, a system for analyzing spatio-temporal data is provided. The system includes a storage element for receiving at least two associated datasets having temporal, spatial, and broadband spectral content and a processing element. The processing element is configured for reducing each of the associated datasets by filtering the broadband spectral content and segmenting each of the reduced datasets into a plurality of patterns utilizing a colorimetric analysis of the reduced datasets. The processing element is further configured for obtaining characteristics of each of the plurality of patterns in each of the reduced datasets, discarding common ones of the patterns from the reduced datasets, and identifying a type of dynamic associated with the remaining ones of the patterns in the reduced datasets.

In some embodiments, the dataset includes neurophysiologic data. In some embodiments, an applying further includes selecting a colorimetric space having a spatial content following the spatial content of the dataset, matching spatial coordinates in the dataset and to spatial coordinates in colorimetric space, and adding colorimetric attributes to the dataset based on the matching.

In other embodiments, segmenting includes localizing phase aggregations in the dataset, identifying local maxima, detecting dynamical transitions based on the identified local maxima, and parsing continuous the dataset into patterns according to the detected dynamical transitions.

In still other embodiments, analyzing includes registering characteristics of each of the plurality of patterns in the dataset, performing a statistical analysis of the plurality of patterns, and classifying the type of dynamics in each of the plurality of patterns based on a taxonomy of patterns. The analyzing can further comprise determining a sequential organization of the plurality of patterns, deciphering a mode of coordination dynamics for each of the plurality of patterns, and estimating a source of observed spatio-temporal activity for each of the plurality of patterns based on the deciphering.

In yet another embodiment, the deciphering further includes creating time-series to model dynamics of at least one among a single sulcal source, a single gyral source, pairs of uncoupled sources, pairs of coupled sources in-phase, pairs of coupled sources anti-phase, pairs of coupled sources at another phase angle, and pairs of sources with meta-stable dynamics. The deciphering also includes applying a forward model to the sequential organization and collecting resulting dynamics at virtual sensors, identifying critical signatures for each case of virtual neurophysiologic signals in terms of frequency dynamics, relative phase dynamics, and amplitude dynamics, comparing characteristics of each of the plurality of patterns with the critical signatures, and inferring an underlying coordination dynamics for each of the plurality of patterns.

BRIEF DESCRIPTION OF THE DRAWINGS

FIG. 4 shows an example of segmentation of continuous EEG into state-transitions.

DETAILED DESCRIPTION

Figure 1A:
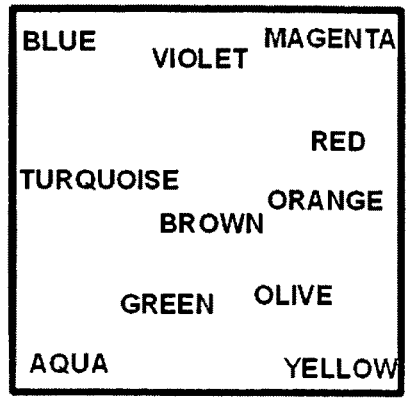
FIGS. 1A-D show exemplary surface colorimetric models for use in the various embodiments of the invention.
Figure 1B:
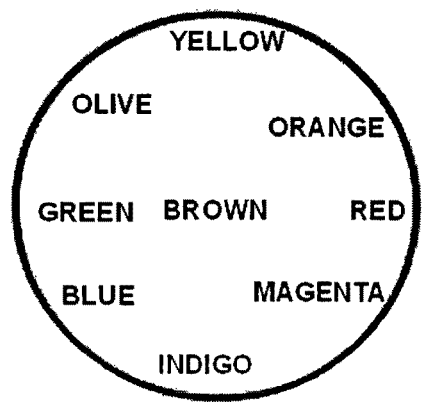
Figure 1C:
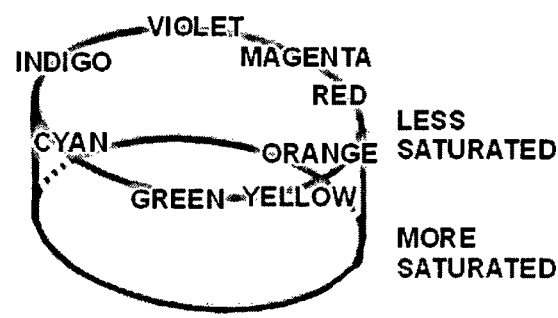
Figure 1D:
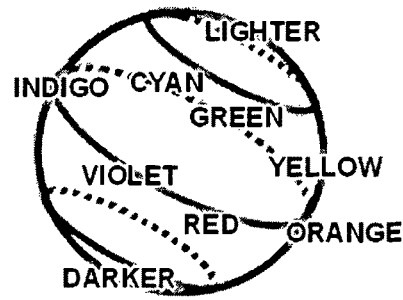
Figure 1E:
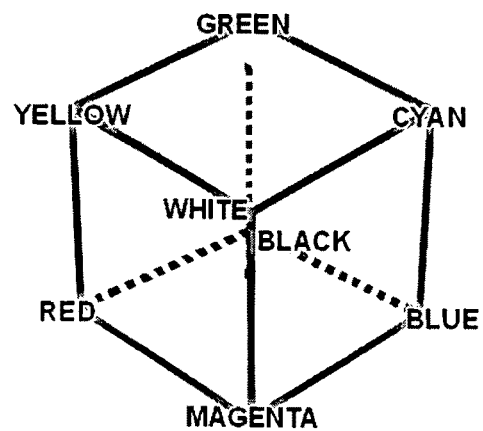
FIGS. 1E-1H show exemplary volume colorimetric models for use in the various embodiments of the invention.
Figure 1F:
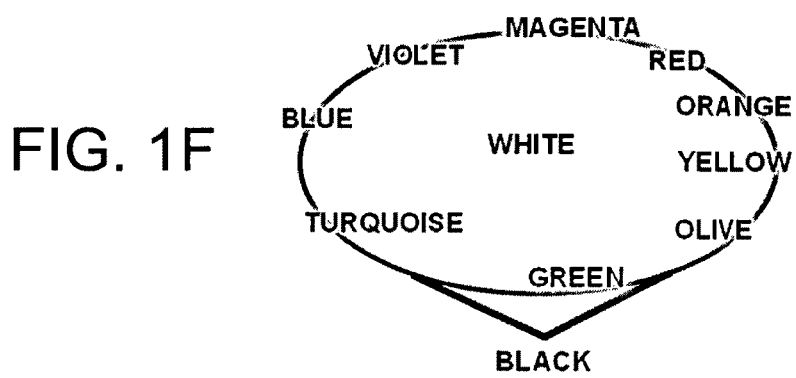
Figure 1G:
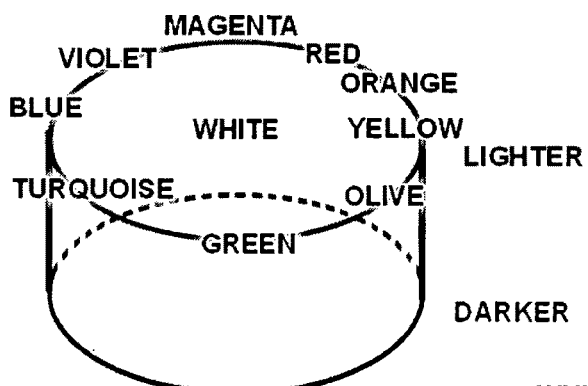
Figure 1H:
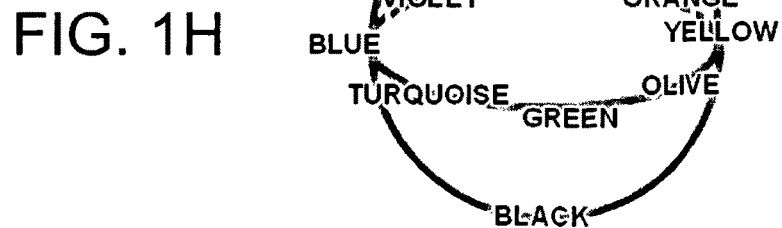

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Overview

Embodiments of the invention provide systems and methods for exploration of high-dimensional datasets, and to allow visualization of 4 or 5-dimensional behavior of a system using a 2 dimensional graph in order to extract meaningful information about the system's functional organization. An exemplary embodiment of the present invention provides a system and method for analysis of the spatio-temporal data: that is, analysis of a dataset that is dependent on measurement location, but also on evolution of the dataset over time. For example, a system with state variable s (1 dimensional) measured in a number of locations at coordinates (x, y, z) (3 or 2 or 1 dimensional) over time t (1 dimensional) is defined. Systems and methods in accordance with embodiments of the invention map the spatial coordinates (x, y, z) with a suitable colorimetric model (a color space that is continuous on 2 or 3 dimensions).

FIGS. 1A-D show exemplary surface colorimetric models for use in the various embodiments of the invention. FIGS. 1E-1H show exemplary volumetric colorimetric models for use in the various embodiments of the invention. In the various embodiments of the invention, the value of the state variable s over time t at each measured location is then plotted with the color that is mapped to that location. As a result of the colorimetric mapping, more information is provided than initially allowed by the two physical dimensions of the support medium thanks to the ability of the perceptual system of the observer to associate color similarity as spatial similarity in the domain (x, y, z). For example, an observer will intuitively understand that data associated with a dark or hunter green color is generally closer to data associated with an olive green color than to data associated with a red color.

As described above, to understand how the brain functions, it is necessary to decipher its spatio-temporal organization as expressed in a suitable analysis of data such as EEG, MEG, ECoG or LFP. Therefore, applying the various embodiments of the invention to brain spatio-temporal datasets allows the functional states of continuous brain dynamics to be read as a comprehensible language and to improve understanding of the functional organization of the brain. As a result, complex aspects of human behavior may be explained that encompass and combine: perception, action, cognition, memory, consciousness, attention, emotion and motivation. Furthermore, it is highly relevant to investigating the diseased brain, with the goal of (a) understanding intrinsic and systemic implications of local dysfunctions and (b)-even more critically—studying brain disorder that are distributed in nature. Finally, it is a pertinent methodological framework to test the effect of therapeutic interventions on the brain and in particular pharmaco-dynamics.

Figure 2A:
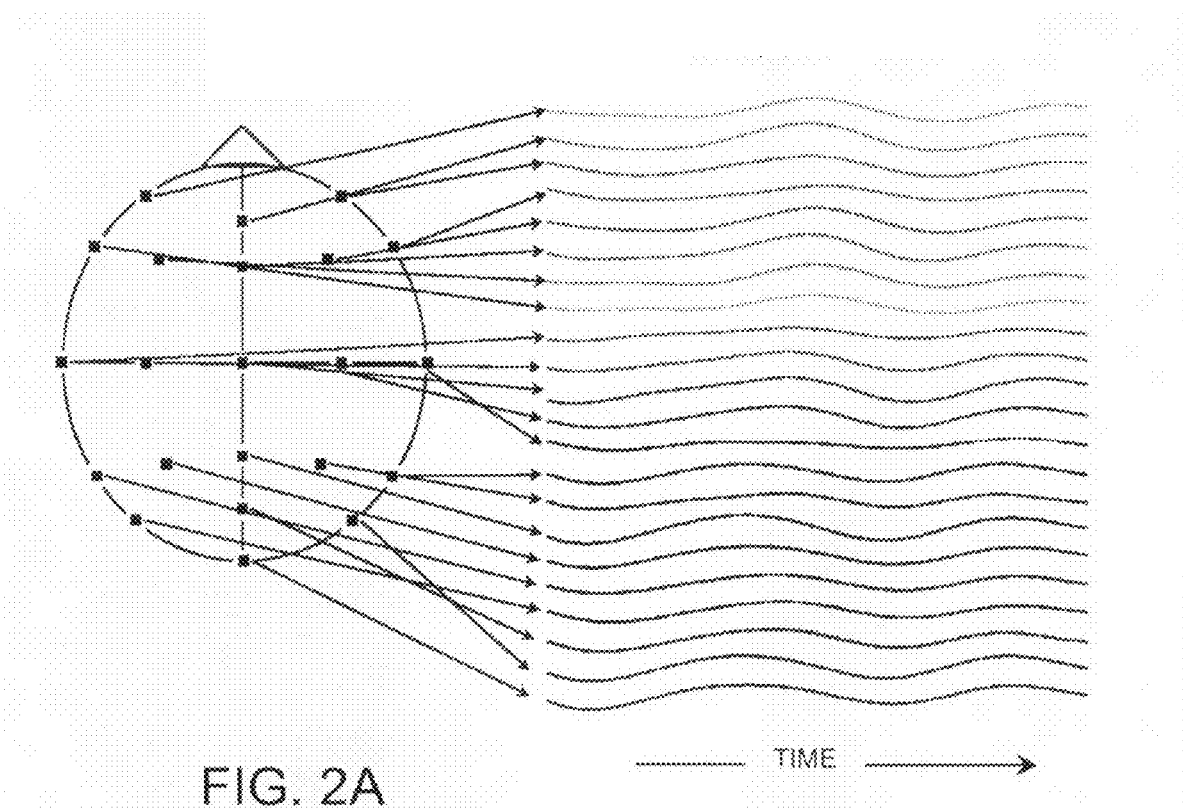
FIGS. 2A-2C illustrate an exemplary 4D visualization of EEG brain waves in accordance with an embodiment of the invention.
Figure 2B:
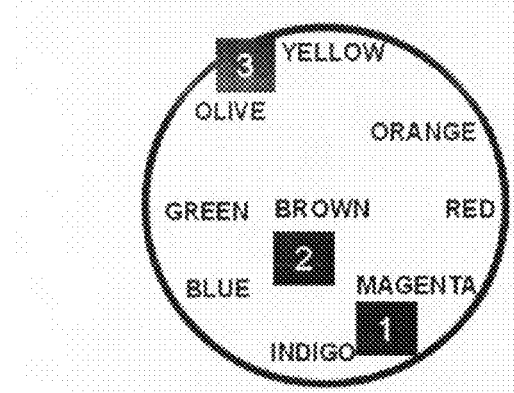
Figure 2C:
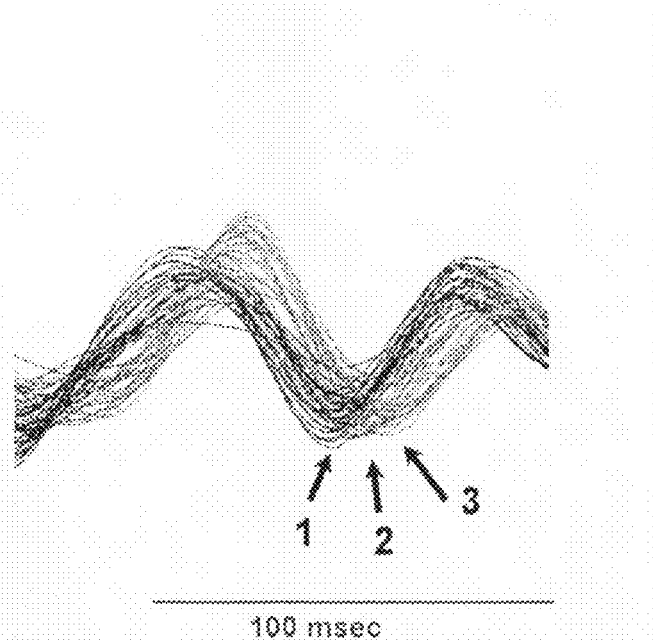

FIG. 2A-2C illustrate conceptually an exemplary spatio-temporal patterning of brain activity in accordance with an embodiment of the invention. FIG. 2A shows brain activity collected from various points on a subject's head during electroencephalography measurements. As shown in FIG. 2A, these result in separate time series. However, if such measurements are combined, it would be difficult for the human perceptual system to understand the data as whole, particularly; it would be difficult for an observer to ascertain how data are grouped in space and in time. However, if the colorimetric map in FIG. 2B is applied to the data in FIG. 2A and the data is then combined, spatio-temporal visualization is provided, as shown in FIG. 2C, which an observer can more intuitively understand. For example, an observer would be able to see that dynamics is driven by three phase aggregations with distinct spatial and temporal properties: (1) locally maximal over occipital right region of the cerebral cortex and with a phase lead; (2) locally maximal over vertex region and with an intermediary phase and (3) locally maximal over left prefrontal region and with a phase lag. The phase aggregations reveal that three neural assemblies participate to the system's function at that particular time.

Although the exemplary embodiments of the present invention provide a system and method for analyzing brain function dynamics, the invention is not limited in this regard. Nor is it restricted to spatial domains of less than or equal to 3 dimensions as adaptations can be made to accommodate hyperspaces. The systems and methods disclosed herein can be also used to investigate the spatio-temporal dynamics in other domains that deal with similar data structure, for instance, but not limited to, the domains listed below.

Going beyond perceptual limitations at 3D and visualizing 4 or 5 dimensions of data in a static 2 dimensional graph could benefit a number of fields in which understanding the spatio-temporal behavior of a system is desired. Some of these fields include: Geology (spatio-temporal seismicity patterns); Population Biology (evolution of a species population over a geographical area); Meteorology (temporal evolution of worldwide sea temperature fluctuations); Physics (temporal evolution of magnetic anomalies on the surface of the planet, evolution of solar activity); Agronomy (evolution of crop productivity on a land, insect monitoring); Biology (development of bacterial populations, dynamics of immune response); Pharmacology (recruitment of binding sites, pharmaco-dynamics); Medicine (dynamics of cardiac cells activity, epileptic seizure propagation, spatio-temporal patterns of gene expression); Epidemiology (spatio-temporal distribution of the flu virus, spatio-temporal distribution of obesity, spatio-temporal distribution of AIDS); Demography (spatio-temporal distribution of income, spatio-temporal distribution of birthrate); Economics (spatiotemporal patterns of industrial output, spatio-temporal distribution of consumer spending); Public policy (spatiotemporal traffic patterns); Material science (temporal evolution of deformation of a solid structure exposed to heat); Chemistry (spatiotemporal patterns of catalytic reactions) . . . etc. Another example of applying the various embodiments of the invention to such types of datasets is shown in FIGS. 3A and 3B.

Figure 3A:
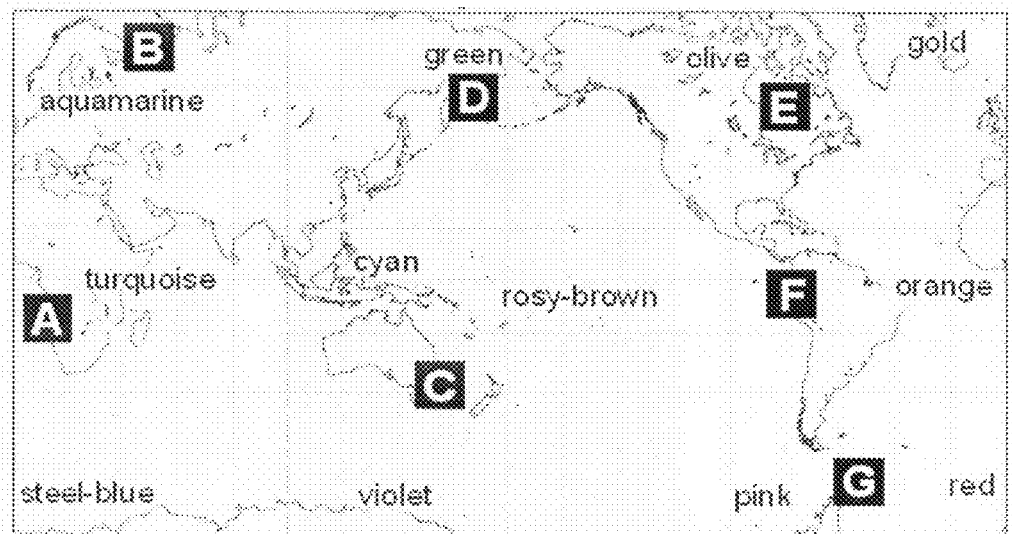
FIGS. 3A and 3B illustrate conceptually, an exemplary spatio-temporal visualization of sea surface temperature data in accordance with an embodiment of the invention.
Figure 3B:
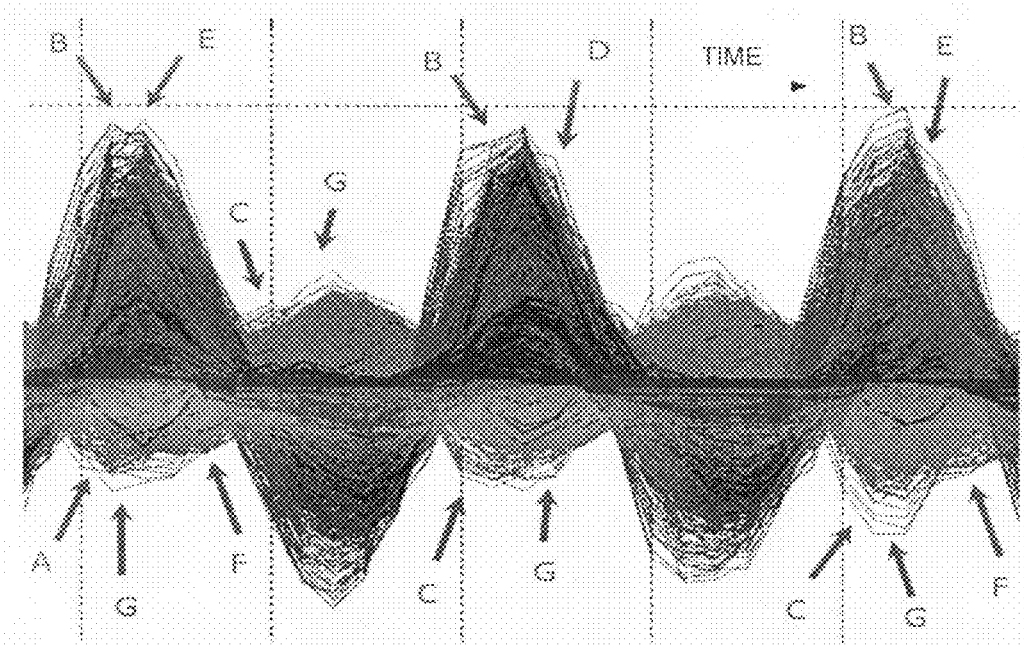

FIGS. 3A and 3B illustrate conceptually, an exemplary visualization of sea surface temperature data in accordance with an embodiment of the invention. FIG. 3A shows an exemplary colorimetric mapping for sea surface data in accordance with an embodiment of the invention. FIG. 3B shows 3 years of the spatio-temporal data visualized with the colorimetric information. It unveils the particular time at which different oceanographic regions will reach their hottest and coolest point; the particular locations that lead the regional trends as annotated with letters A to G; and it exposes the difference in season amplitude, for instance those seen between northern and southern hemisphere. As in the example in FIGS. 2A-2C, the colorimetric mapping permits the observer to have a more intuitive understanding of the variation in sea surface temperatures over time and geographic regions.

In oscillatory systems, such as those shown in FIGS. 2 and 3, one important feature to examine is the occurrence of phase aggregations from neighbor locations (x, y, z) in the temporal trajectories of the state variable (s(t)). Local maximum (spatio-temporal point that dominates a phase aggregation) are identified, such as the maxima occurring in FIGS. 2C and 3B.

By using such colorimetric techniques in the various embodiments of the invention, dynamical system analyses can be performed more effectively. A dynamical (spatio-temporal) analysis aims to understand how the system evolves in time. Over a given period of time, the system may be stationary (its spatiotemporal organization continuing/repeating thorough the time interval); it may obey state/transitions (its spatio-temporal organization exhibiting abrupt changes); or it may be meta-stable (exhibiting stationary transient behavior in which integrative tendencies and autonomy co-exist) amongst other.

In the case of non-stationary dynamics, a further aspect of the invention is to segment the succession of homogenous dynamics occurring over time. Based on the features identified using colorimetric mapping in accordance with the various embodiments of the invention, such transitions in data can be more easily detected or observed. This is conceptually illustrated with respect to brain function dynamics in FIG. 4. FIG. 4 shows a combined plot of electroencephalography data of a subject over time, colorimetrically mapped in accordance with an embodiment of the invention. A transition occurs when the temporal organization of phase aggregations changes, for instance one phase aggregate disappears, or a new phase aggregate appears. In FIG. 4, three dynamical states are shown in boxes, A, B, and C, each separated by an abrupt change in dynamics. In A, two phase aggregates, green and magenta are observed. In B, the magenta phase aggregate disappears and two new phase aggregates (blue and orange)

appear. In C, blue and green phase aggregates recede while a purple and a second orange phase aggregate emerge. The result of this analysis is the segmentation of the continuous dynamics of the system in a succession of k homogeneous episodes (states or dwells) that may further be the object of a description, statistical analysis and classification.

Classification of the sample in a suitable taxonomy can be performed for each one of the k states found to compose the entire dataset if it is non-stationary or for the entire dataset if it is stationary.

A further step consists of identifying the properties that best describe the functional organization of the dynamical state. It includes feeding the attributes of the entire dataset (if it is stationary) or of each of its k pattern (if it is not) into a database on the purpose of performing descriptive statistics. After that, a statistical comparison can be performed if a normative database exists or if more than one group of spatio-temporal observations is obtained.

The regions of local maxima are generally of interest in understanding underlying rules governing the system. Using instantaneous measures of dynamics (for instance frequency and relative phase for a system governed by oscillatory dynamics), analysis of the sparser set of data composed with the temporal trajectories of the local maxima reveals what is the status of their mutual interaction: for instance whether local-maxima are co-active but independent, or phase-locked, or engaged in meta-stable regimes. Episodes of phase-locked coordination (or functional coupling or transient synchronization) and quasi phase-locked (meta-stable) episodes are especially important in the domain of brain dynamics as they are believed to be the cause of integrative brain function. With the colorimetric mapping provided in the various embodiments of the invention, detection of regions engaged in (quasi) phase-locked coordination becomes more efficient as compared to conventional techniques. For example, conventional techniques addressing functional coupling in the brain typically employ a combinatorial set of cross-correlation measures (or their derivative) between all pairs of recording sites. This technique generally generates an unpractical quantity of data to analyze (pair-wise analysis aggravate the size of the problem at a rate of factorial n!; e.g. for 128 recording sites, already 8128 pairs need to be dealt with). Furthermore, since the resulting dataset can not only include spatio-temporal observations regarding real coordination but many other observations that only express spurious coordination the ability to distinguish between the two cases may be lost in the enlarged dataset resulting from conventional techniques. In contrast, in an analysis performed in accordance with an embodiment of the present invention the mass of data is screened through first, and then only a meaningful set of observations is subjected to further analysis. Observed dynamics of the local maxima can be compared to results of some forward models to identify if the observed features match those of real synchrony.

In addition to the coordination problem above, there can also be a question regarding the sources of the observed activity (i.e., the "inverse problem"). This question arises because recording sites (e.g., scalp for EEG recording) and sources (e.g., groups of pyramidal neurons in the grey matter of the cerebral cortex) are in two distinct spaces. As a result, mathematical estimation of the locations originating an observed signal typically needs to be performed. Generally, such a question is said to be ill-posed (for each distribution of observation, there is an infinite number of possible source configuration). To address such problems, source estimation is generally performed to minimize the infinite set of solutions to a unique, most probable one. This conventional technique uses prior and optimization techniques to do so. Such source estimation methods employ either one time point or an arbitrary time windows to proceed to source estimation. In the later case, more comprehensive information about the spatio-temporal behavior of the system is inputted, but there is a large risk that several temporally discrete episodes of brain dynamics are blended into the analysis, causing it to fail in recognizing the sources and their proper coordination dynamics. For instance, if source estimation is performed on data such as shown in FIG. 4, an arbitrary window of 500 msec upon which source estimation is performed may happen to include portions of pattern A, pattern B and pattern C. In contrast, the patterns obtained from segmented EEG are ideal data samples to perform such a sensitive analysis because only one pure episode of brain dynamics is fed to the source estimation algorithm (e.g. from FIG. 4, one can isolate pattern B, irrespective of its precise onset, offset time and duration).

Colorimetric Mapping

Figure 5:
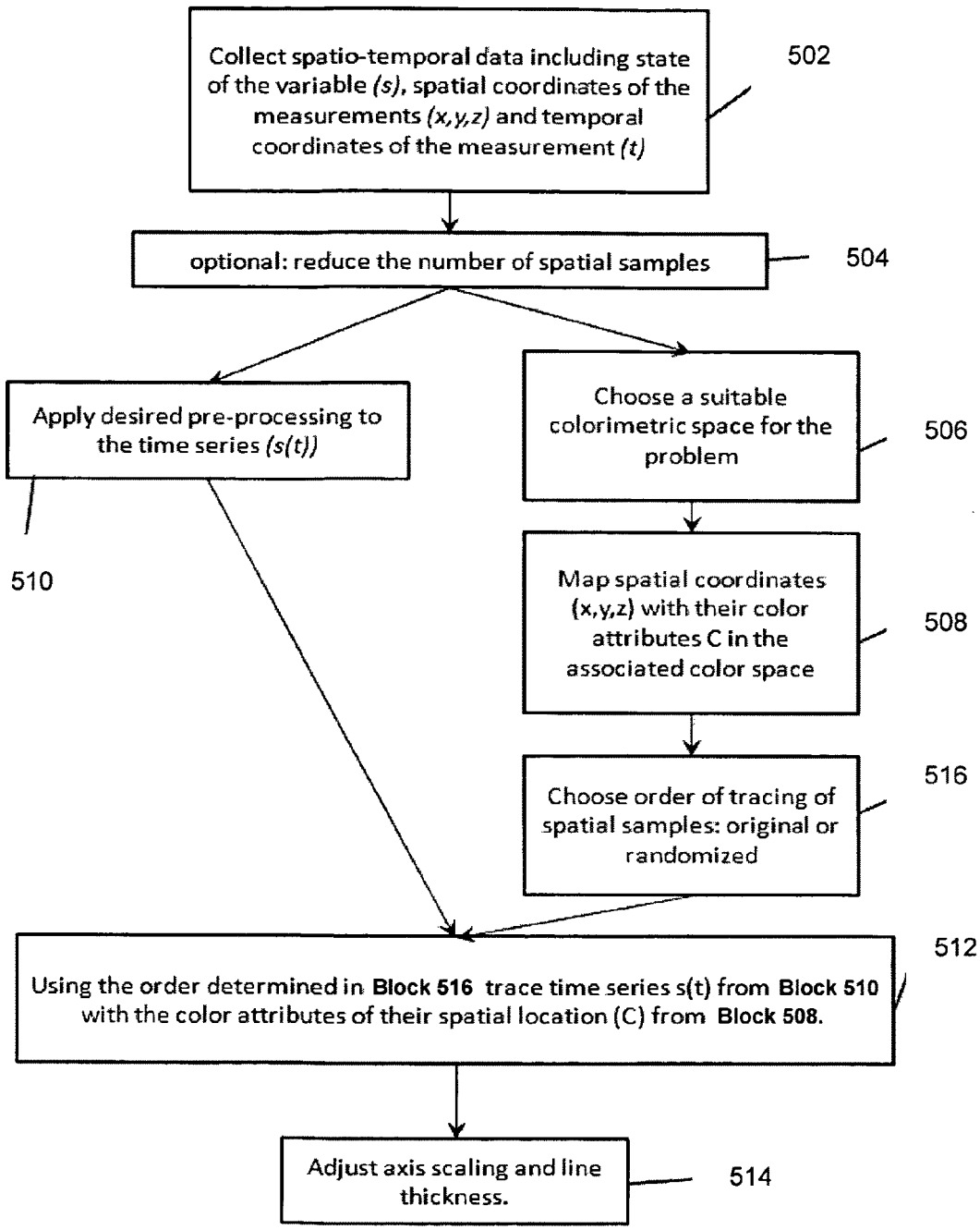
FIG. 5 shows steps in an exemplary method to visualize a 4 or 5 dimensional dataset in accordance with an embodiment of the invention.

To overcome the various limitations in displaying of spatio-temporal data using conventional plotting or graphing methodologies (i.e., to break beyond perceptual limitations at 3 dimensions), embodiment of the invention unlock the spatial frame of the system from its rigid coordinates and transfer the notion of spatial location/proximity (in the aforementioned domain x, y, z) into color attributes and/or color similarity. The is illustrated in FIG. 5. FIG. 5 shows steps in an exemplary method 500 for applying a colorimetric model to a spatio-temporal or other 4 or 5 dimensional dataset in accordance with an embodiment of the invention. Method 500 begins at block 502 with the collection of spatio-temporal data, including state variable (s), spatial coordinates (x, y, z) and temporal coordinates (t). In block 504, the user can decide to display all the spatial samples, or only a subset, for purposes of improving the legibility of the graph.

Once the dataset is collected at block 502 (and optionally reduced at block 504), a suitable colorimetric model is chosen for the spatial format of the problem at block 506. In the various embodiments of the invention, the colorimetric model can be a surface, such as a square, a disk, a tube or a sphere, as shown in FIGS. 1A-1D; or it can be a volume, such as a cube, a cone, a cylinder or a ball, as shown in FIGS. 1E-1H. In general, the color space can be chosen to represent features of the system (for instance Cartesian, polar, spherical) and to optimize the perceptual abilities of the observer by selecting the largest color span and a distribution in which color distance is identical in all directions of the model. After the proper color space is chosen at block 506, measurement taken at every location from the original system are attributed a color-code mapping that of the corresponding region in the colorimetric space at block 508.

Data pre-processing of time series can be performed prior to visualization to emphasize aspects of the spatio-temporal data at block 510. The type of pre-processing depends on the problem being investigated. For instance, if periodic or seasonal features are studied, a filter may be performed (as done in FIG. 2) in order to eliminate concurrent periodic processes as noise. If fluctuations rather than magnitude are a concern, de-trending can be applied as in FIG. 3.

Afterwards, at block 512, the temporal trajectories of all measurements are displayed with this color encoding, and spatial organization from the original data emerges as color organization in the graph, such as in FIGS. 2C and 3B. For any observer with normal color vision, the spatio-temporal patterning of the system is revealed quasi-instantaneously and intuitively.

Successful visualization of the spatio-temporal patterning is based on perceptual color grouping (gestalt). A certain density of spatial samples is required for the spatio-temporal patterning of the system to be clearly perceived. A minimum of 16 sites is recommended for a system with 2 dimensions of space. If a dataset has a small number of spatial samples, but if the conditions of a spatial Nyquist are met, then some suitable spline or interpolating functions may be used to augment spatial density.

The scaling of the colorimetric figure should also be adapted to favor the color-gestalt. If the colorimetric figure dimension is large in comparison with the number of spatial samples, there will be a large gap between temporal trajectories of neighbor regions and the gestalt may be compromised. Accordingly, after the display of data is generated at block 512, parameters of line thickness and colorimetric figure dimension can be adjusted according to the number of spatial samples at block 514 to improve understanding and perception of the dataset.

In some cases, the number of spatial samples can be very large in comparison with the dimension of the figure. As a result, the likelihood increases that trajectories traced first and being in the lowest layers of the plot may be occluded by trajectories traced last and being on the upper layers of the plot. Consequently, the information conveyed by the earliest traced spatial samples may be lost. Accordingly, in some embodiments of the invention, method 500 can be adjusted to for large numbers of spatial samples. For example, prior to tracing or displaying the dataset at block 512, the order of tracing of spatial samples can be adjusted at block 516 so that no region of the system is systematically hidden in the lowest layers of the figure. The ordering can be performed in a pre-defined or random manner. In some embodiments, if conditions of spatial Nyquist are overreached, spatial down-sampling can be used to adjust the dataset to improve visualization further as in block 504.

Analysis of Spatio-Temporal Data

Figure 6:
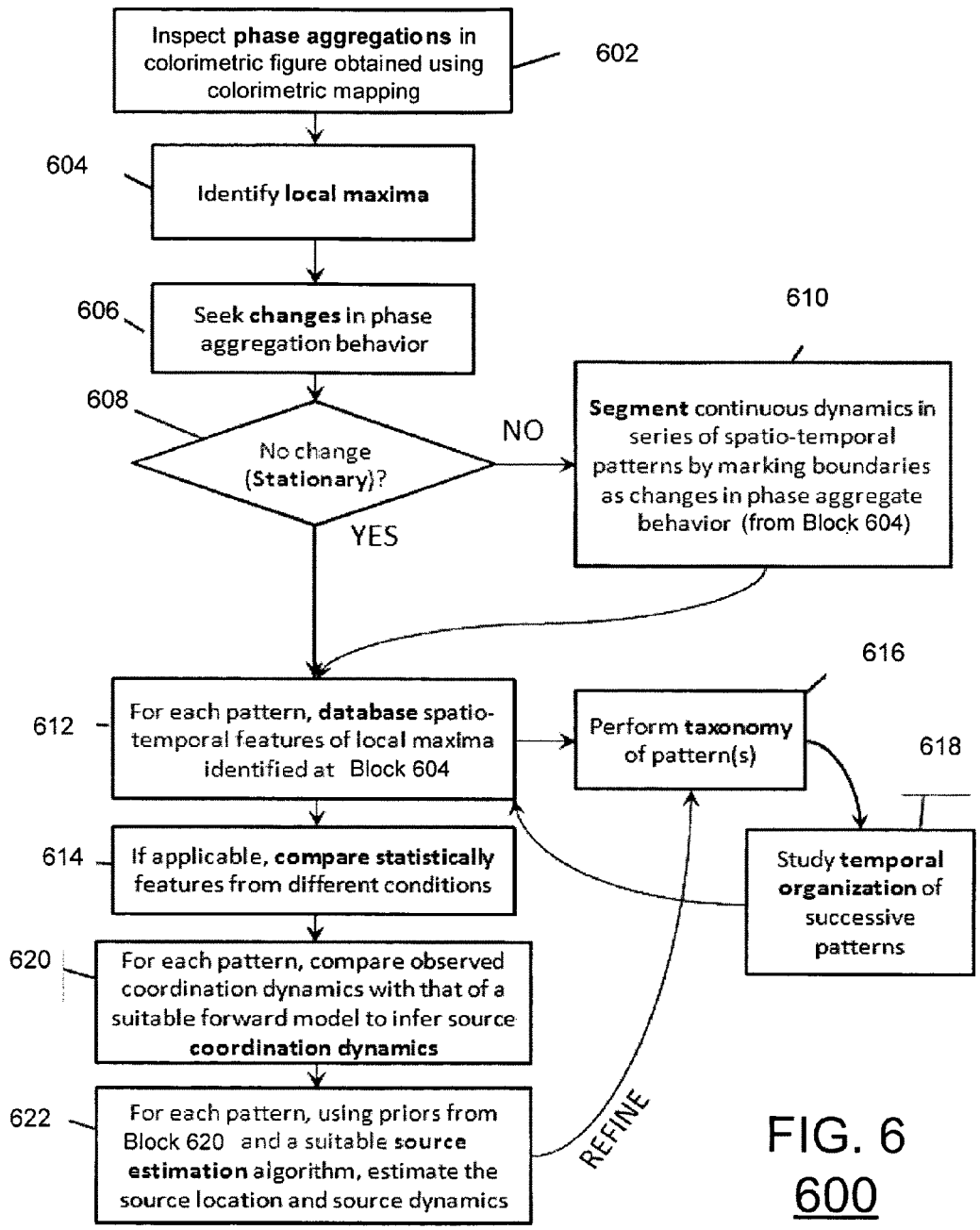
FIG. 6 shows steps in an exemplary method for analyzing a system's behavior in accordance with an embodiment of the invention.

As described above, in addition to colorimetric mapping, another aspect of the invention includes analyzing the spatio-temporal dynamics of the system. Although spatio-temporal data can be analyzed in several different ways, an analysis in accordance with the various embodiments of the invention can take advantage of the features resulting from the colorimetric mapping. FIG. 6 shows steps in an exemplary method 600 for analyzing a system's behavior in accordance with an embodiment of the invention. Although method 600 is shown as incorporating several steps, one of ordinary skill in the art will recognize that parts of method 600 can be employed in isolation, depending on the context of the dataset. Furthermore, although the steps in method 600 will be described with respect to studying brain dynamics, this is for illustrative purposes only and method 600 can be used for analysis of any type of multivariate data. As described below, FIG. 6 describes several main processes for analysis of spatio-temporal data: basic analysis and segmentation, description of system properties and statistical analysis, taxonomy, inferences on coordination dynamics, and source estimation.

Basic Analysis and Segmentation

Method 600 begins at block 602 with the inspection of phase aggregations obtained from a colorimetric mapping and plotting, such as one resulting in a dataset mapped using method 500 in FIG. 5. This is followed by the identification of local maxima at block 604 based on the phase aggregations. For a system exhibiting an oscillatory dynamics such as brain activity measured with EEG, the spatio-temporal organization takes the form of phase aggregations, as illustrated in FIGS. 2C and 3B. Phase aggregations express the decay of variable (s) over space (x, y, z) from a local maximum through neighboring locations. As long as the system continues over time with the same spatio-temporal organization, for instance if phase aggregations continue or repeat regularly, then the system is in the same dynamical state. If a change in phase aggregation (or other quantity relevant for the system) is observed, then a transition has occurred. Accordingly, at block 606, any changes in phase aggregation are then identified. These changes can be used at block 608 to determine whether the system is not stationary.

If the system is not stationary as identified at block 608, segmentation at block 610 is accomplished by identifying the temporal points at which ongoing dynamics changes and by marking a transition at each of these points. When segmenting the continuous dynamics of a high-dimensional dataset into states and transitions, care has to be taken to emphasize meaningful changes in the dynamics and to ignore meaningless change that may nonetheless have massive impact on quantitative probes of the system dynamics (and consequently obscure or overwhelm meaningful changes). In that respect, support of the visualization method is valuable to identify what are the tangible elements of the problem and where redundancy is present. The present segmentation method is not based on changes beyond threshold in global statistical estimates of the entire dataset, but rather, it focuses on targeted changes involving the local maxima specifically (definition of this meaningful change depending on the specific problem at hand). For instance in the domain of EEG segmentation, neural groups will exchange information during episode of transient phase synchronization and then will desynchronize, marking a transition to a new neural assembly. Accordingly, the investigator is due to ignore all the statistical changes that co-vary with amplitude and frequency fluctuations however massive, and focus solely on change in the phase arrangement of the local maxima (as previously shown in FIG. 4). In another sort of problem, such as epileptic seizure propagation, shown in FIG. 7, synchronization may be instrumental in the spread of abnormal activity: in turn, emphasis is given to the recruitment of new spatial sources irrespective of their phase relationships.

Figure 7:
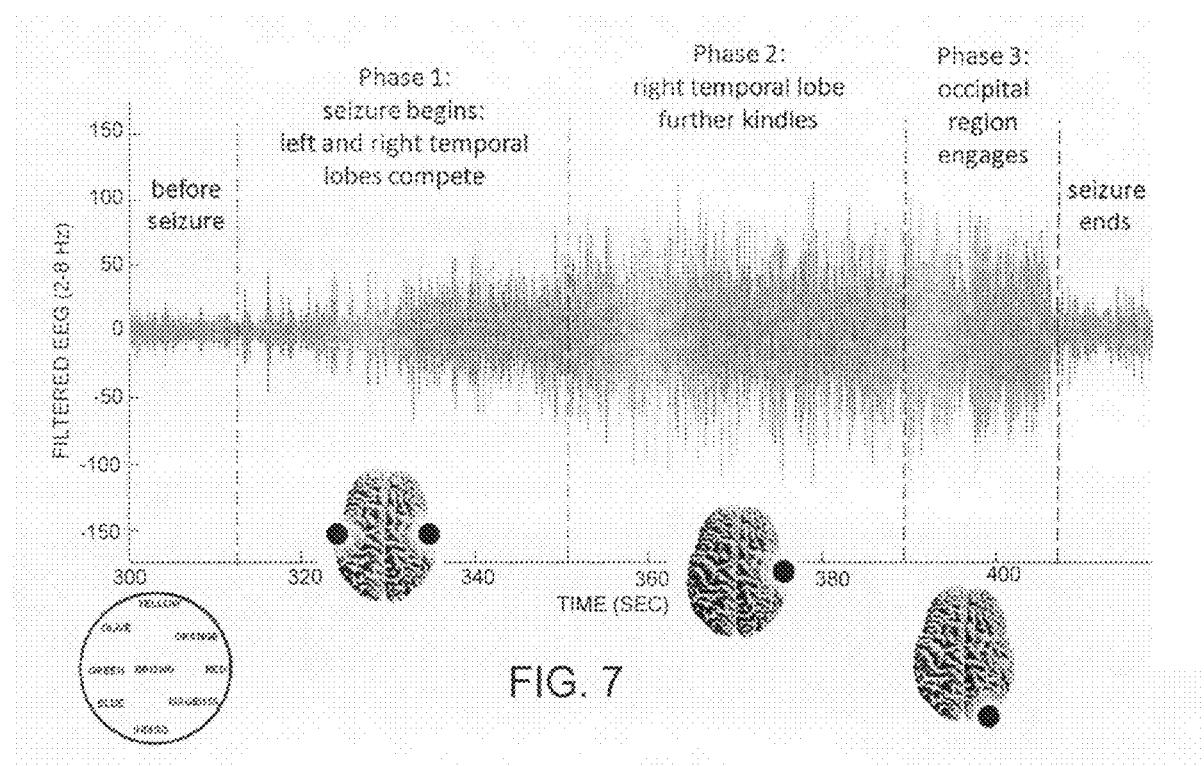
FIG. 7 shows how segmented EEG data from an epileptic seizure can be entered in an ad hoc taxonomy in accordance with an embodiment of the invention.

FIG. 7 shows an EEG plot in accordance with an embodiment of the invention, illustrating seizure propagation during the various phases of an epileptic seizure. The dataset is segmented in three critical phases as confirmed with colorimetric visualization that include (phase 1): a phase of growing activity involving both left and right temporal lobes; (phase 2): a phase of stabilization at high amplitude of right temporal activity alone; and (phase 3): the engagement of right occipital region leading to the termination of the seizure.

Whereas the segmentation method at block 610 may yield results that are similar to that of other segmentation methods in particular instances, it is based on different principles: working in concert with a visualization method in accordance with the embodiments of the invention has the flexibility to allow selective aspects of the problem and core regions of the spatio-temporal dataset to be focused upon.

Description of System Properties and Statistical Analysis

Referring back to FIG. 6, for the entire spatio-temporal sample if the system is stationary over the temporal interval under consideration (no transition observed) as determined at block 608, or for each of the k samples if it is not, the analysis continues to block 612 for registration of the spatio-temporal features describing the behavior of the system. That is, specifying parameters are registered into a database. In the case of brain dynamics, meaningful properties may include {local maxima of phase aggregates, circumstance of occurrence, onset time, offset time, duration, phase stability, mean relative phase, mean relative frequency—and for each local maximum: mean amplitude, integral of the amplitude, mean frequency, frequency variance}. 'Circumstance of occurrence' refers to relevant descriptors for the investigation: group of observation, task, behavioral, cognitive or clinical parameters during which brain patterns arise.

When several groups of observations are compared, the content of this database may be subjected to a statistical analysis at block 614 to identify which patterns significantly differentiate the groups. For example, a pattern of brain activity may have statistically different amplitude before and after treatment and be a neuromarker of successful therapy. As a possible outcome of this statistical analysis, patterns that do not significantly differ between the groups of observation can be discarded. Patterns that do differ can be subjected to further analysis. Additionally a taxonomy of the patterns can be performed at block 616, as described below.

For non-stationary datasets as determined at block 608, it is desirable to identify temporal organization of the successive patterns as determined at 618 for each recognizable member of the taxonomy as performed at block 616. For instance in the domain of EEG, some patterns have affinity to appear in succession of one another, probably as a result of hidden functional determinism that one is precisely trying to uncover. If a pattern alpha is observed repeatedly to precede the occurrence of a pattern beta, a temporal dependency is suggested, that can be further established by a quantitative analysis.

To study temporal dependency organization at block 618, a temporal vicinity is defined (e.g. 500 msec before and after each pattern; or 2 ranks before and after each patterns), and for each lag/interval composing this vicinity, the probability distribution of neighbors is computed. Cells with high probability generally reveal temporal dependency between different states of the system.

Taxonomy

Transient dynamical states observed in the dataset may be samples of a recurring functional organization, and may repeat if the system is observed over a sufficiently long period of time. In that case, at block 616 each pattern may be assigned to a discrete class that represents a specific functional organization of the system. If the dynamics are stationary, or non-stationary but with a small number of patterns, this class may be the output of a dedicated classifier. In the case of non-stationary dynamics with a large number of patterns, classification may also be performed on the basis of an ad-hoc taxonomy of the system's states. Examples of such classes in the domain of EEG are phases of sleep; subcritical, intercritical or critical phases of an epileptic brain; or spatio-temporal patterns that express a cognitive or behavioral function as determined ad-hoc during an investigation. Referring back to FIG. 7, if the three phases of epileptic seizure are observed recurrently, the behaviors described in those three particular segments of EEG data can be generalized as a taxonomy of epileptic seizure propagation, and the corresponding class may further be evaluated and used in a descriptive or predictive manner.

In the case of EEG, it should be noted that classes defined a priori on the "raw" EEG signal are liable to two issues of spatial equivalence and contextual spatial shift. Spatial equivalence refers to the fact that two distinct configurations of brain sources can originate similar scalp patterns as measured with EEG. With more descriptors of the dynamics (phase relationship, frequency, amplitude, etc. . . . ), the problem of spatial equivalence may be greatly minimized but not completely eliminated. Contextual spatial shift refers to changes in the spatial properties of a scalp pattern when its originating source is observed in isolation or in the context of other ongoing activity. Or in other words, patterns with distinctly different appearance may come from partially identical underlying brain networks.

Resolution of both issues can be completed after successful source estimation, as described below in reference to block 622. Source estimation opens up the possibility to refine the classification at block 618 by uncovering functional heterogeneity in a class (reassign spatio-temporal pattern to distinct elements of the taxonomy); and by uncovering functional homogeneity between samples of two different classes (merge two classes in a combined element of the taxonomy). However, the segmenting and classification at blocks 610 and 618, respectively, are useful contributors to improving source estimation at block 622. Therefore, in some embodiments of the invention, a first pass on classification is performed and the classification is refined after source estimation.

Inferences on Coordination Dynamics

The coordination dynamics of the system can be inferred at block 620. That is, the observed coordination dynamics can be compared to a suitable model to estimate or infer coordination dynamics of sources underlying the system dynamics. The importance of this step owes to the fact that function of a complex system is always accompanied by collapse of its dimensionality: parts of the system are enrolled into working together and the dynamics they produce looses degrees of freedom in the process of gaining order. Such a behavior is observed in systems with strong and weak coupling alike (albeit with different degrees of dimensionality reduction), and accordingly, coordination dynamics is a pervasive feature of all elements in nature.

Reading of coordination dynamics is not direct because of many spurious manifestations in spatio-temporal data that takes the same appearance as real coordination. A modeling approach is undertaken, in which all possible source behaviors are considered in a conceptual model of coordination dynamics and hypothetical time series are generated accordingly; dynamics of such sources are fed to a computational forward model to simulate resulting observable time series; and signatures in those model output that discriminate real and false synchronization are identified and compared with sample data.

Figure 8:
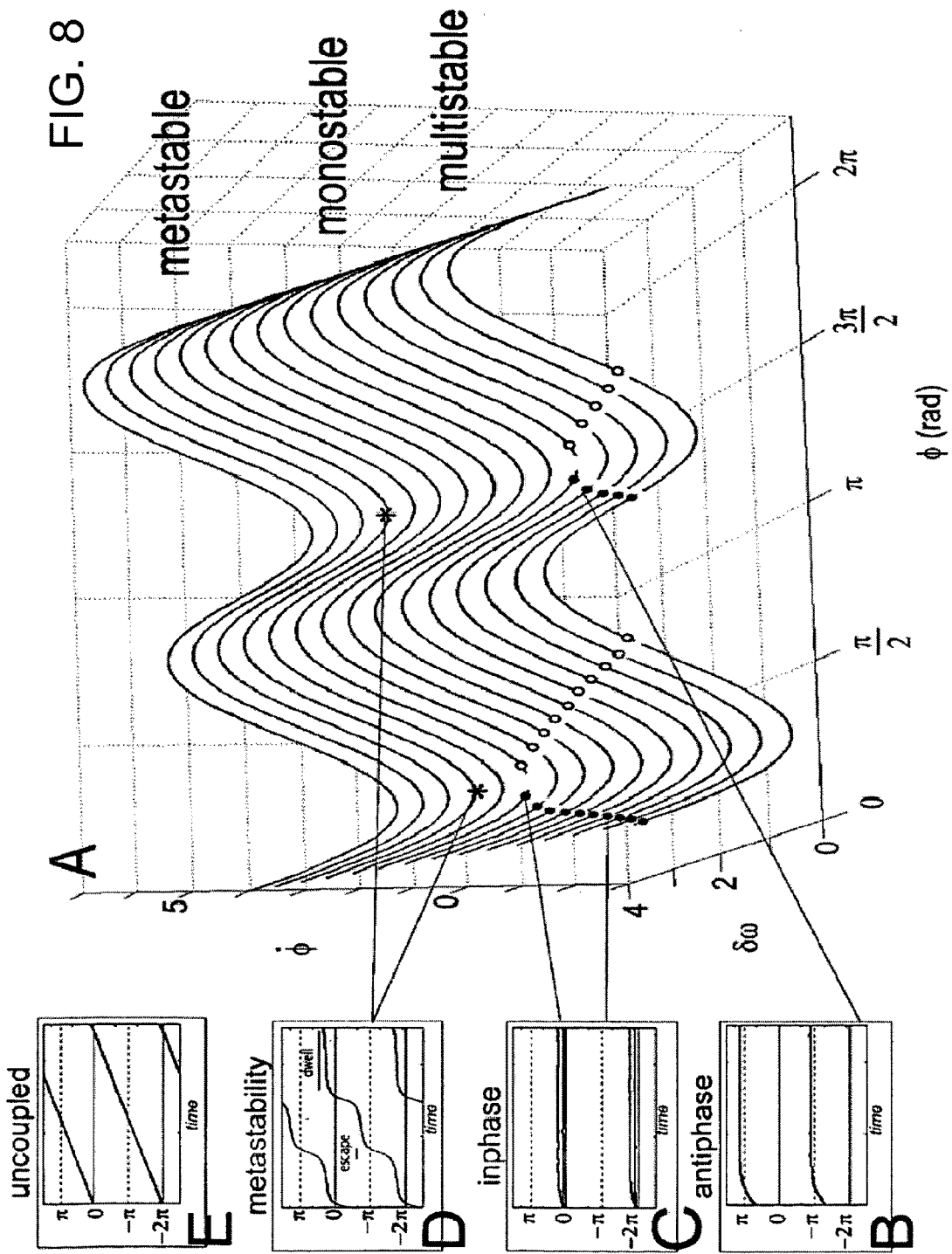
FIG. 8 is a theoretical model of brain coordination dynamics that is used to specify functional behaviors upon which forward models are based.

For example, in the case of EEG analysis, a model of coordination dynamics for various oscillations can be used, such as the model in FIG. 8. FIG. 8 is a theoretical model of brain coordination dynamics that exhibits multi-stability, adaptive phase shifts, critical phase transitions and meta-stability. Each source element is capable of intrinsic oscillation. The key collective variable that characterizes the coordination between source elements is the relative phase. (A) shows the flows of the relative phase ($\phi$) for varying parameter values of $\delta\omega$ (difference between each element's intrinsic oscillatory frequency) and for fixed coupling values. Boxes show the corresponding phase behavior as a function of time. Flow lines passing through $d\phi/dt=0$ define the fixed points of the coordination dynamics (places where the rate of change of the relative phase is null). Stable fixed points (attractors) are shown as filled circles; unstable fixed points (repellers) as open circles. Red flow lines are multi-stable: depending on initial conditions, trajectories of the relative phase are attracted near anti-phase (B) or in-phase (C, red). When the pair of fixed points near anti-phase collides and disappears, a bifurcation occurs to the mono-stable regime in which the relative phase is exclusively attracted near in-phase (C, blue). Green flow lines (A) belong to the meta-stable regime. All the fixed points have disappeared and only "remnants" remain. Coordinative tendencies emerge with successive dwellings near in-phase and anti-phase (D). For reference, relative phase of uncoupled sources is shown in (E).

Figure 9:
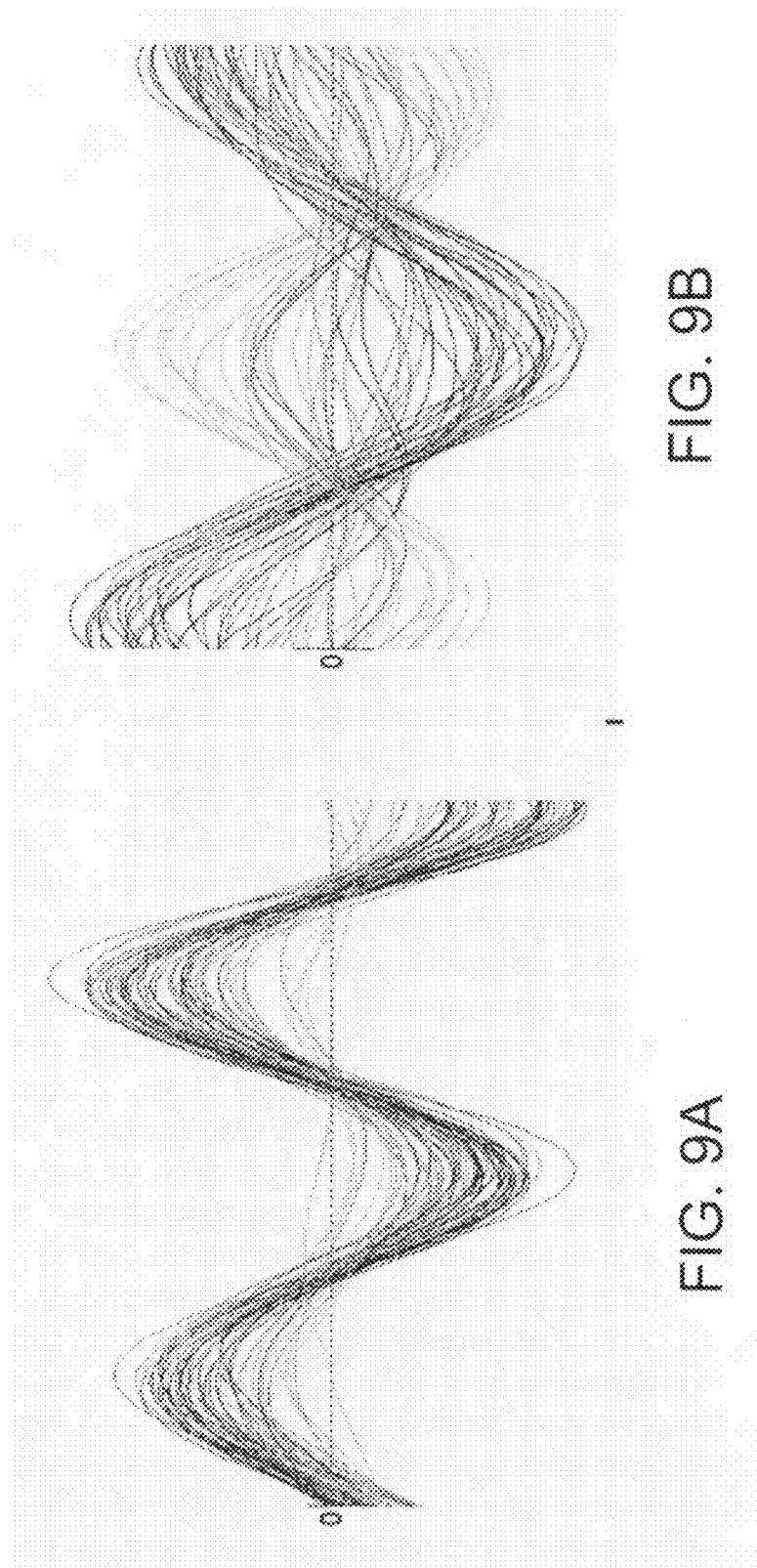
FIGS. 9A and 9B shows radial (A) and tangential (B) patterns arising from single sources.
Figure 10:
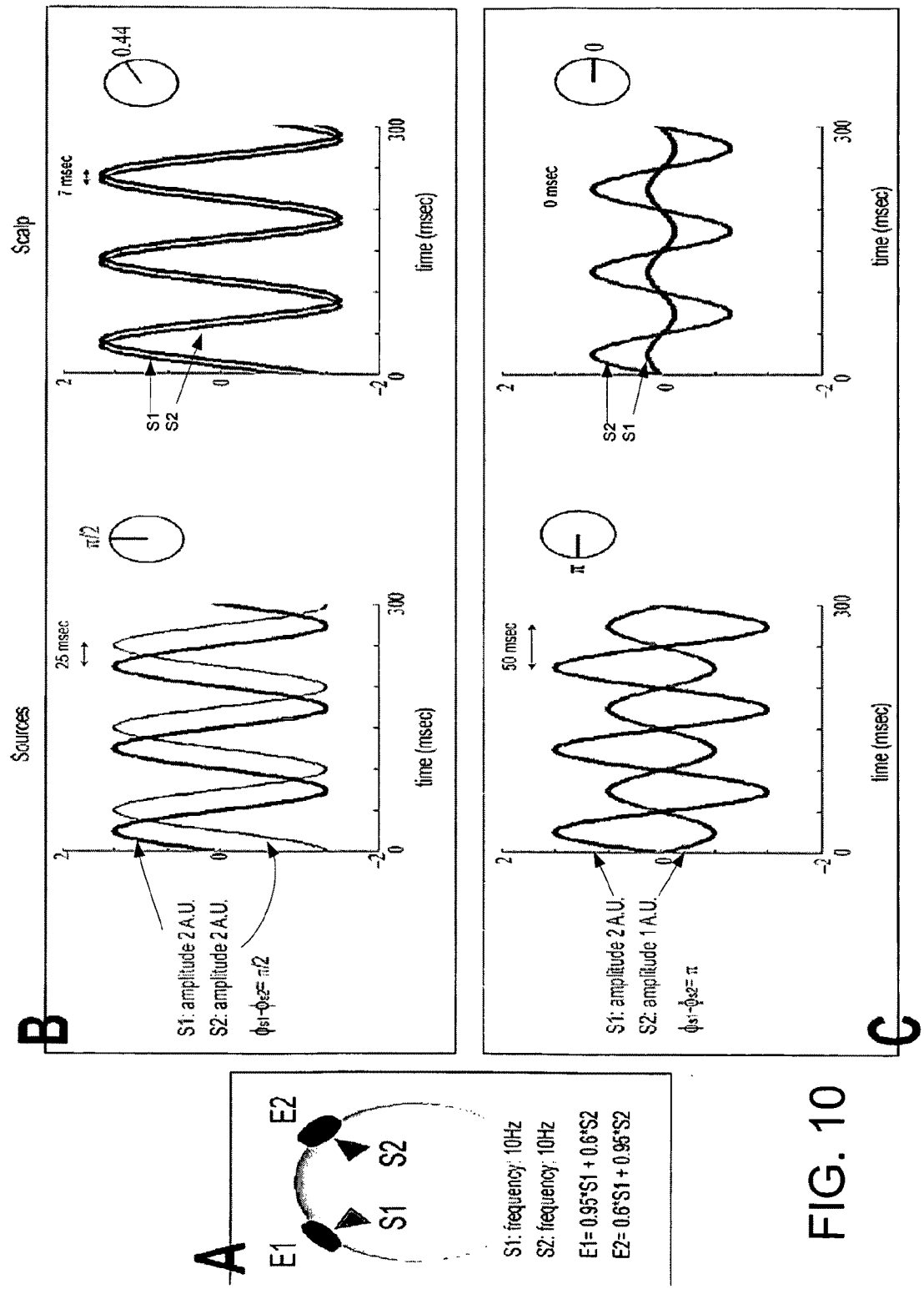
FIG. 10 shows distortion of apparent phase during phase locked states in a model.

This model specifies the relative phase dynamics of coupled oscillations for given parameters of the system. It indicates that coordination between brain oscillations can be observed as: strict in-phase locking, strict anti-phase locking, locking with an angle (a fixed value which is neither in-phase nor anti-phase), adaptive phase transitions and meta-stability. However, in addition to the case of coordinated oscillations, there are cases in which scalp dynamics result from single dominant sources, or from co-active areas which are not phase-locked. Consequently, scalp patterns can conform to 7 basic types of source dynamics or a combination thereof:

a single source dominates the signal, its radial orientation yielding a mono-polar scalp projection. Resulting scalp signal shows spread of activity aggregated at a single phase (apparent in-phase). FIG. 9A shows the resulting pattern observed with the colorimetric mapping. There is one single phase aggregate that oscillates in time, and it decays spatially from its local maximum in the frontal right region (seen with color orange) to reach values close to zero in the occipital left region (seen with color blue).

a single source dominates the signal, its tangential orientation yielding a dipolar projection on the scalp. Resulting scalp signal shows two phase aggregates at a lag of half a cycle from one another (apparent anti-phase). FIG. 9B shows the resulting pattern observed with the colorimetric mapping. There are two phase aggregations with opposing polarity in the frontal left region (seen with color lime green) and in the occipital right region (seen with color purple)

sources coupled in-phase underlie the signal. Resulting scalp signal shows one phase aggregate at in-phase with or without spatial discontinuity depending on source position and orientation and the sensor density.

sources coupled anti-phase. Resulting scalp signal shows two phase aggregates (anti-phase) or one phase aggregate (in-phase) depending on the source's proximity and relative strength, as shown in FIG. 10 and Table 1 below. FIG. 10 shows distortion of apparent phase during phase locked states, especially severe at anti-phase. (A) summarizes the model with sources S1 and S2 oscillating at 10 Hz. (C) shows that beyond a threshold of amplitude asymmetry, source patterns anti-phase (left) flip to scalp patterns in-phase (right) with no passage through intermediary phases. For comparison, (B) shows progressive phase distortion for sources with symmetrical amplitudes that are coupled with a relative phase of $\pi/2$ radians. Table 1 provides:

TABLE 1

Bias in phase of recorded EEG signal

|  | Sources in-phase | Sources anti-phase | Sources at other phases |
|---|---|---|---|
| Same amplitudes Different amplitudes | Scalp in-phase | Scalp antiphase Scalp anti-phase (small difference) until flip to in-phase (larger difference) | Scalp relative phase biased toward in-phase |

Figure 11:
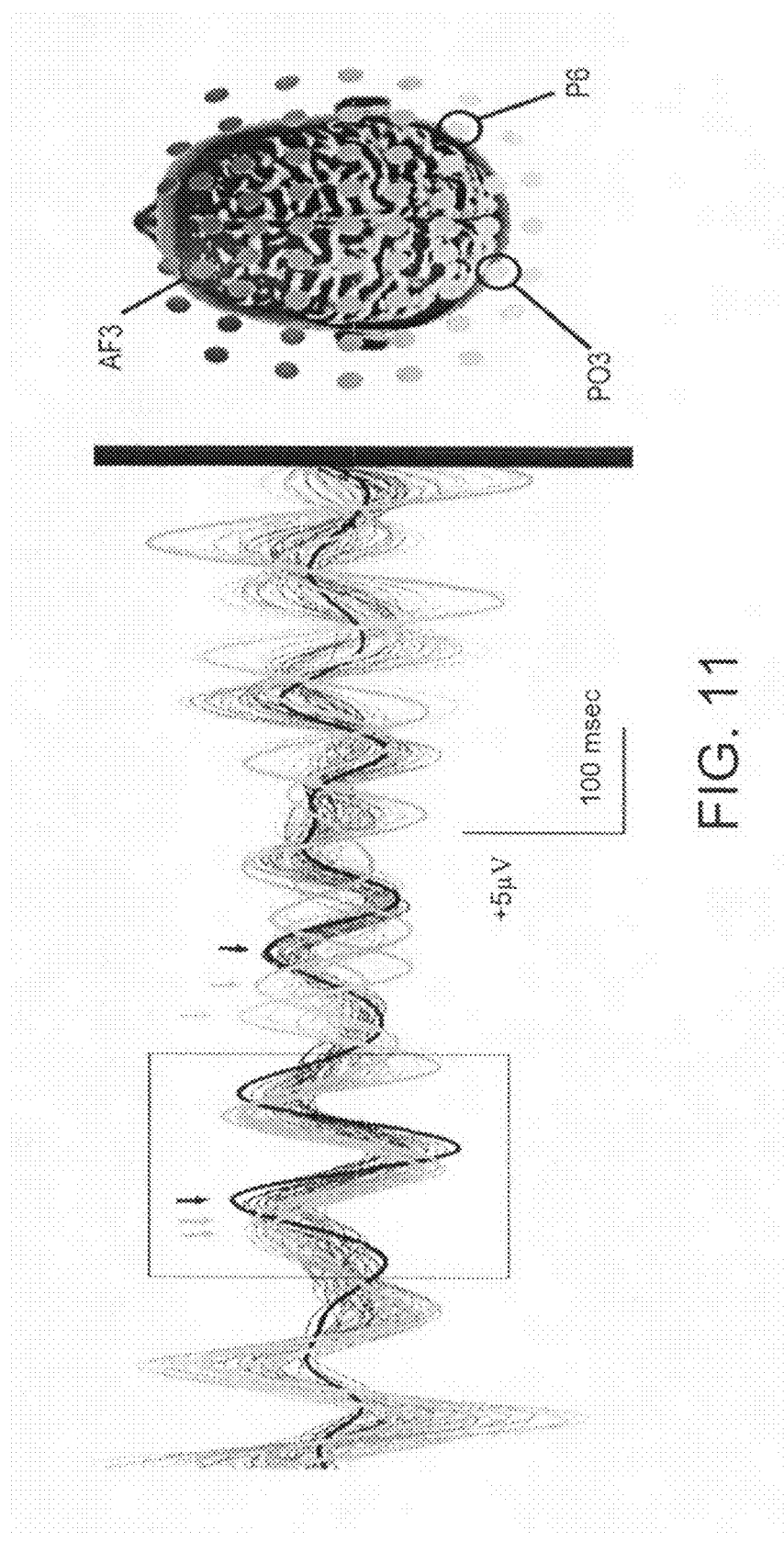
FIG. 11 shows an example of real synchrony between oscillations at three recording sites suggesting that three cortical sources are engaged in coordinated behavior.
Figure 12:
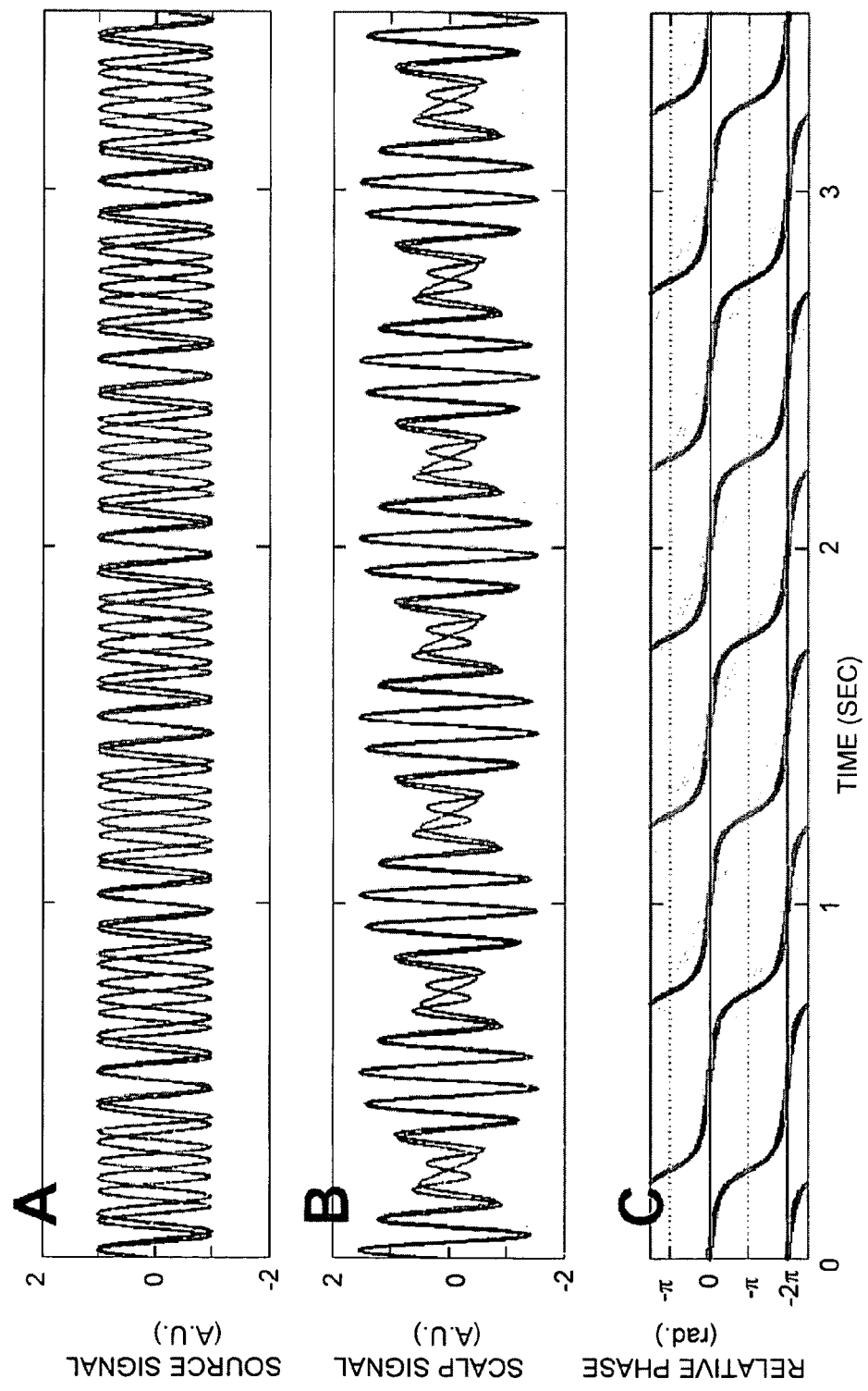
FIG. 12 shows the spurious dwelling of the relative phase observed for two uncoupled sources.
Figure 13:
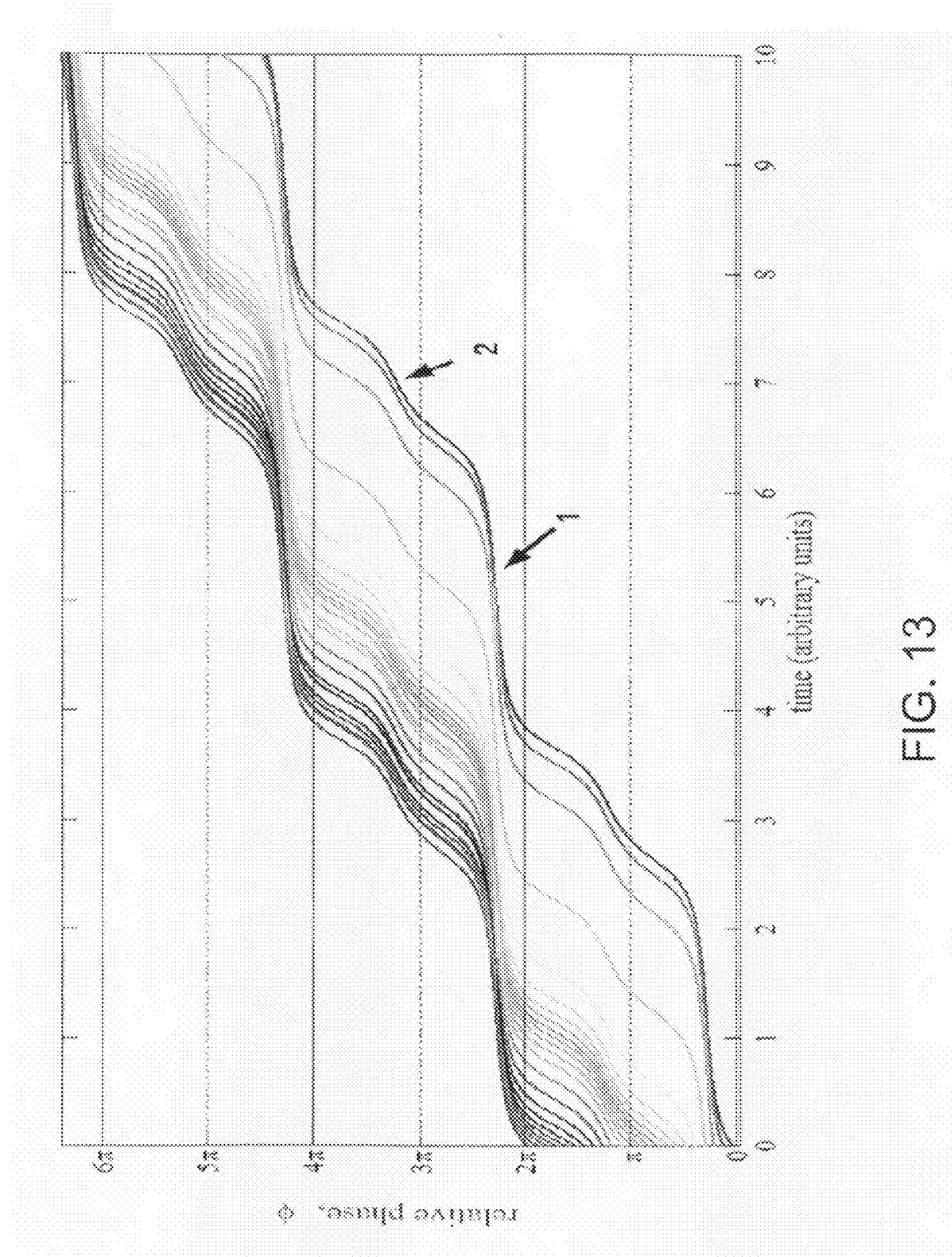
FIG. 13 shows temporal trajectories of the relative phase in a model of metastable coordination dynamics.

As shown above in Table 1, apparent relative phase at the scalp is determined by source relative phase and amplitude asymmetry. For comparison purpose, in-phase and other phase are shown in the table. In-phase is the only pattern whose relative phase is always left true at the scalp. All other relative phases between sources tend toward in-phase at the scalp. Most severe bias is incurred to anti-phase patterns: their phases are preserved for small values of amplitude asymmetries but shift their apparent phase relationship to strict in-phase beyond a critical amplitude asymmetry with no passage to intermediary phase values.

sources coupled at an angle, as shown in FIG. 11. FIG. 11 shows an example of short-lived phase-locked episode (white/black box) between 10 Hz oscillations at three recording sites located above left parietal-occipital, right parietal and left prefrontal areas suggesting that three cortical sources are engaged in coordinated behavior. Phases aggregate near electrodes bearing maximal amplitude at PO3 ($1^{st}$ arrow colored blue), P6 ($2^{nd}$ arrow colored magenta) and AF3 ($3^{rd}$ arrow colored green). Resulting scalp signals show phase aggregates with an angle between them which is neither zero nor pi radians, that can safely be recognized as true coordination between participating brain regions.

sources uncoupled. Resulting scalp signal shows absence of frequency locking. Dwelling is observed intermittently, centered about zero radians and occasionally pi radians, as shown in FIG. 12. FIG. 12 shows the dwelling of the relative phase observed for uncoupled sources. The sources were animated with steady dynamics at 10 Hz and 12 Hz respectively as shown in (A). (B) shows that apparent signals at the scalp exhibit dynamical phase distortion. (C) discloses the genuinely drifting relative phase of the sources (yellow, light grey) and the spuriously lingering relative phase observed at the scalp (green, dark grey).

sources in a meta-stable regime: Resulting scalp signals show intermittent locking; observations are shifted from zero or pi radians, as shown in FIG. 13. FIG. 13 shows ten temporal trajectories of meta-stable regime with different initial conditions. Conversely to the dwell observed in the case of uncoupled source (above), all the meta-stable trajectories dwell at a position over the y-axis which is neither zero nor pi radians.

In the domain of EEG, there is some under-determination of the coordination dynamics from the standpoint of immediately observable properties of measured spatio-temporal activity. To minimize under-determination, the coordination dynamics of observed patterns can be compared to a predictive model (conceptual model of EEG, model of spatial correlation or forward model, or a combination of all three). Hints are provided by the visualization method in accordance with the various embodiments of the invention. For instance, source orientation is manifest in the spatial decay of phase aggregates, with spatial decays which are strongly nonlinear indicating the presence of a tangential source (this feature due to the curvature of the head). Especially important hints may be obtained from the study of how the spatio-temporal patterns begin and terminate. While states occupy most of the spatiotemporal data, they are less important than transitions to understand the system: the manner with which a transition occurs (scattering, disappearing, reorganization within the same set of phase aggregates or reorganization with new functional elements), supports the understanding of underdetermined aspects of the system coordination dynamics. Yet, not all uncertainty will be systematically reduced and inference of coordination dynamics will take the form of inference and likelihood.

Figure 14:
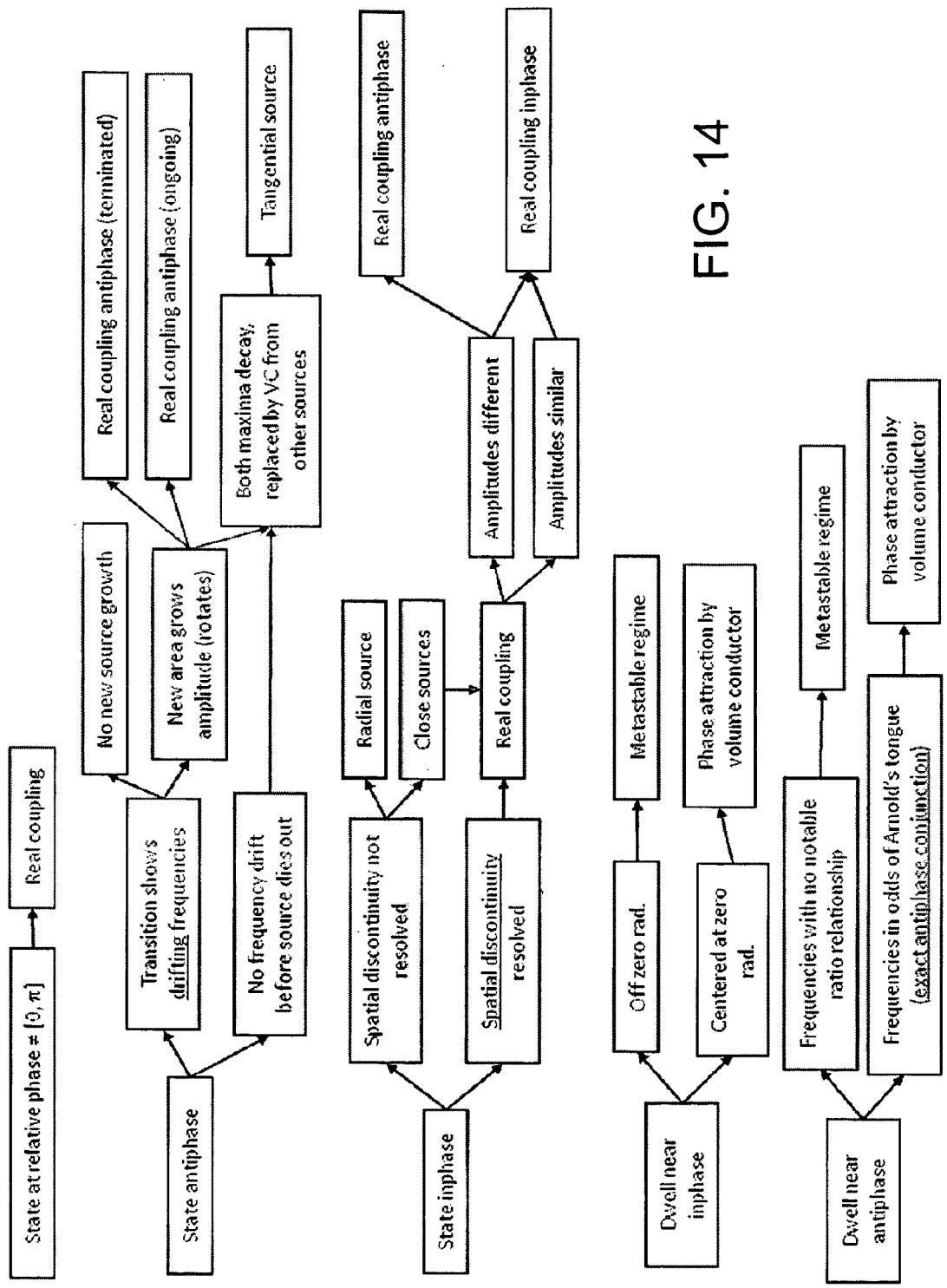
FIG. 14 shows a decision tree used to infer EEG source coordination dynamics on the basis of EEG raw signal attributes.

In some embodiments a decision tree, such as the one shown in FIG. 14 for recognizing the source coordination dynamics on the basis of raw signal attributes, provides the potentiality and likelihood of each source configuration to produce a given set of spatiotemporal observables. The outcome of this analysis is a formal description of the coordination dynamics of spatio-temporal patterns. For instance, it may be shown that a pattern involving two synchronized brain areas is present during perception of simultaneity between a visual and auditory stimulus, and absent when stimuli are perceived as asynchronous. Or it may be shown that the amplitude of a pattern is diminished for increased concentration of a therapeutic agent, and that this pattern engaged a single brain area.

Source Estimation

Referring back to FIG. 6, if anatomical attribution is desired, or in an attempt to refine the output of the classification, source estimation techniques that are suitable for "single-trials" or continuous EEG may be performed at block 622. This process of source estimation can be aided by several key aspects of the present method: (a) homogeneous sample of brain activity is fed to the source estimation process, maximizing the chances of its successful convergence in comparison with single trials with arbitrary temporal limits or evoked potential, (b) preprocessing of EEG as bandpass filtering limits inter-electrode variance in Signal-to-Noise-Ratio and artifacts, and (c) source estimation is constrained by prior knowledge of the underlying dynamics (number of sources and mode of interaction) as determined at block 622.

Additional Exemplary Embodiment

In another exemplary embodiment of the present invention, a system and method are provided for comparing (intra-group, intergroup) brain dynamics observed under two or more circumstances, for instance differences in brain activity: (a) before and after a treatment is applied; (b) for evolving concentration of a therapeutic molecule; (c) between a baseline (rest) state and a cognitive or behavioral task; (d) between a reference period and the period of onset of a behavioral, cognitive or clinical transition (e.g. seizure); (e) between two cognitive or behavioral tasks; (f) between successive investigations of a clinical group at evolving stages of a disease; (g) between a healthy control group and a clinical group; (h) between two or more clinical populations, to name a few. This is illustrated in FIG. 15.

Figure 15:
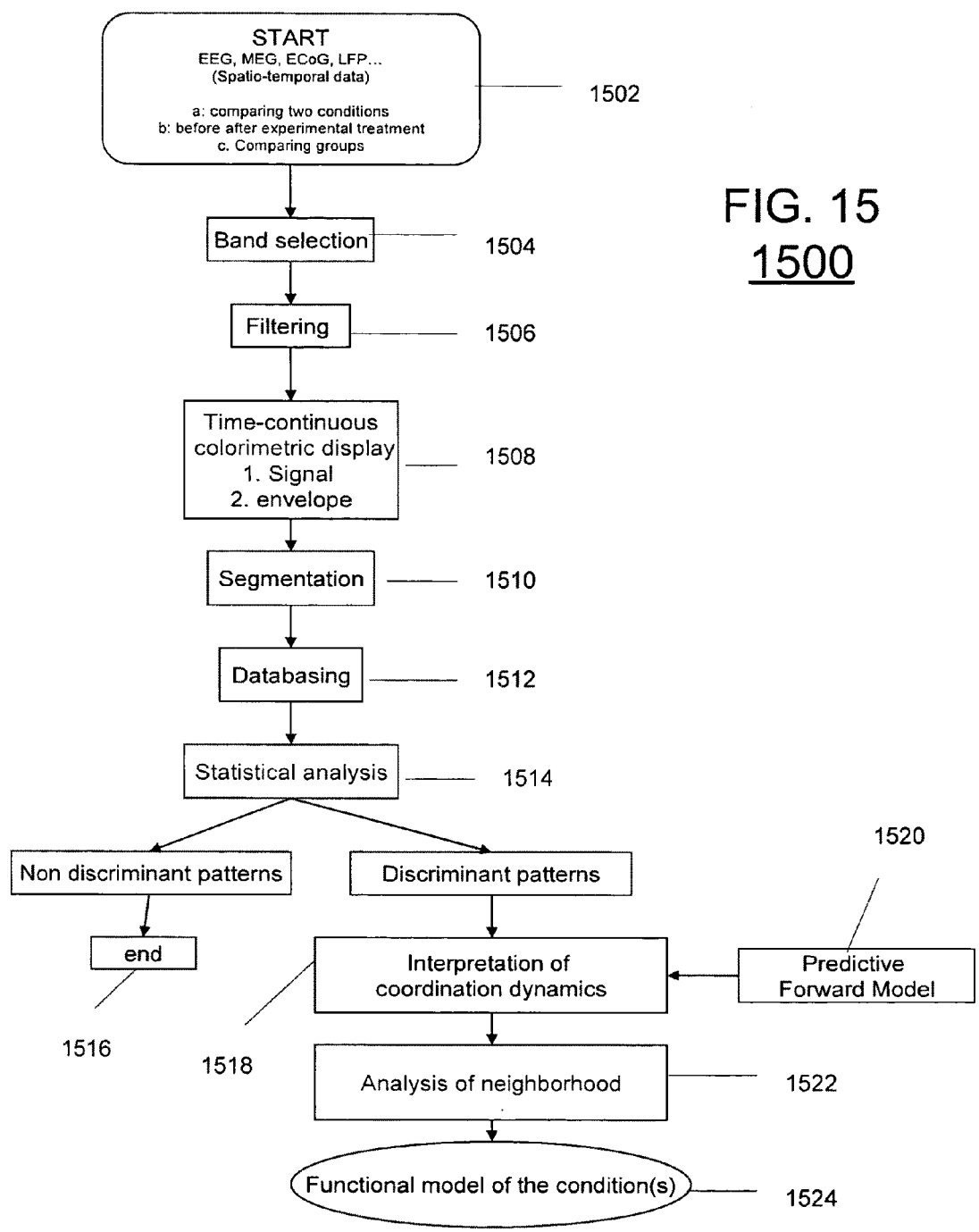
FIG. 15 shows steps in an exemplary method for comparing brain dynamics in accordance with an embodiment of the invention.

FIG. 15 shows steps in an exemplary method 1500 for comparing brain dynamics. Method 1500 begins at block 1502 by collecting neurophysiologic data. In the various embodiments of the present invention, any neurophysiologic data, including, but not limited to EEG, MEG, ECoG, or multichannel LFP, can be used. The data can be collected using multiple sensors covering the 1-D or 2-D spatial domains under investigation (scalp surface, square section of cortical surface, alignment domain of a multi-contact deep electrode). In some embodiments, at least 5 sensors for 1-D arrays and at least 16 sensors for a 2-D array. For each observation group (e.g. before and after treatment), resulting data takes the form of a N×M matrix, with N being the number of sensor and M being the number of time samples.

After the data is collected at block 1502, is a reduction of the broadband spectral content of the neurophysiologic signals is performed at block 1504. This is achieved by band pass selection and/or filtering. A multitude of filter techniques can be applied, with the precaution that signal phases should be preserved. The passband of the filter is chosen either in an exploratory manner (e.g. method applied successively to different bands); on theoretical grounds (e.g. relevance of a frequency band for a task or clinical state) or ad hoc on the basis of discriminant brain activity observed between each observation group (the use of a colorimetric spectrum is then recommended to guide the band selection). Afterwards, at block 1506, a digital filter can be applied, where the digital filter does not introduce a phase shift in the data.

Once the data is filtered, colorimetric mapping is applied at block 1508. This can be according to method 500 or another method. Afterwards, a segmentation of the neurophysiologic signals on the basis of their spatio-temporal patterning with the help of colorimetric mapping can be performed at block 1510. In block 1510, a visualization interface is formed with the display of time-continuous filtered neurophysiologic signals on the top, and on the bottom, the display of the envelope of the signals. The successive patterns are identified. Boundaries are placed at the occurrence of waning points of the envelope for each spatiotemporal pattern. The activity of a source may span several patterns if other sources are recruited and superpose during the course of its existence. The outcome of this stage is a series of k spatio-temporal patterns of size N×D(k) (with D(k) duration of the pattern k).

After segmenting at block 1510, the properties of each pattern are registered or databased in a database at block 1512. For each pattern k, the parameters registered are {local maxima of phase aggregates, circumstance of occurrence, onset time, offset time, duration, phase stability, mean relative phase, mean relative frequency—and for each local maximum: mean amplitude, integral of the amplitude, mean frequency, frequency variance}. 'Circumstance of occurrence' describes relevant descriptors for the investigation: group of observation, task, behavioral cognitive or clinical parameters during which neural patterns arise.

After registering or databased at block 1512, a statistical analysis is performed at block 1514 that identifies which patterns significantly differentiate the groups of observations. For example, a pattern may have statistically different amplitude before and after treatment. The outcome of this step is that patterns that do not significantly differ between the two groups of observation are discarded. Patterns that do differ are subjected to further analysis. Afterwards, the dynamics that underlie the patterns of interest are further scrutinized. The theory of Coordination Dynamics specifies the relative phase dynamics of coupled oscillations for given parameters of the system. It indicates that coordination between brain oscillations can be observed as: strict in-phase locking, strict anti-phase locking, locking with an angle (a fixed value which is neither in-phase nor anti-phase), adaptive phase transitions and meta-stability. In addition to the case of coordinated oscillations, there are cases in which scalp dynamics result from single dominant sources, or from co-active areas which are not phase-locked. Consequently, scalp patterns conform to the basic types of source dynamics described above.

Once the statistical analysis is performed at block 1514, discriminant and non-discriminant patterns are identified. For non-discriminant patterns no further analysis is performed and method 1500 ends at block 1516. For discriminant patterns, analysis can proceed at block 1518 with the interpretation of coordination dynamics in the data.

The coordination dynamics of the patterns can be recognized at block 1518 on the basis of signatures provided by predictive forward modeling at block 1520. The outcome of this analysis is the formal description of the properties of spatio-temporal brain activity patterns that differentiate the groups of observations. For instance, it may be shown that a pattern involving two synchronized brain areas is present during perception of simultaneity between a visual and auditory stimulus, and absent when stimuli are perceived as asynchronous. Or it may be shown that the amplitude of a pattern is diminished for increased concentration of a therapeutic agent, and that this pattern engaged a single brain area.

Once the patterns are recognized at block 1518, analysis of neighborhood can be performed at block 1522 to identify temporal dependency between successive patterns: for instance a certain pattern that always follows another, or a pattern which amplitude is systematically increased when preceding another pattern. The probability distribution of neighbors within this time interval is formed for each pattern. Once this analysis is complete, a functional model of the conditions can be derived: a succession of processes can be defined and quantified at block 1524 (task dependent patterns with their spatio-temporal parameters, their established coordination dynamics, inferred functional significance and temporal organization.

If anatomical attribution is desired, the inverse methods may be performed that are suitable for "single-trials". Note that source estimation is aided by patterns' filtering (limits inter-electrode variance in SNR and artifacts), homogeneity of brain activity (in comparison with an Evoked Potential), and by prior knowledge of the underlying dynamics (number of sources and mode of interaction).

Figure 16:
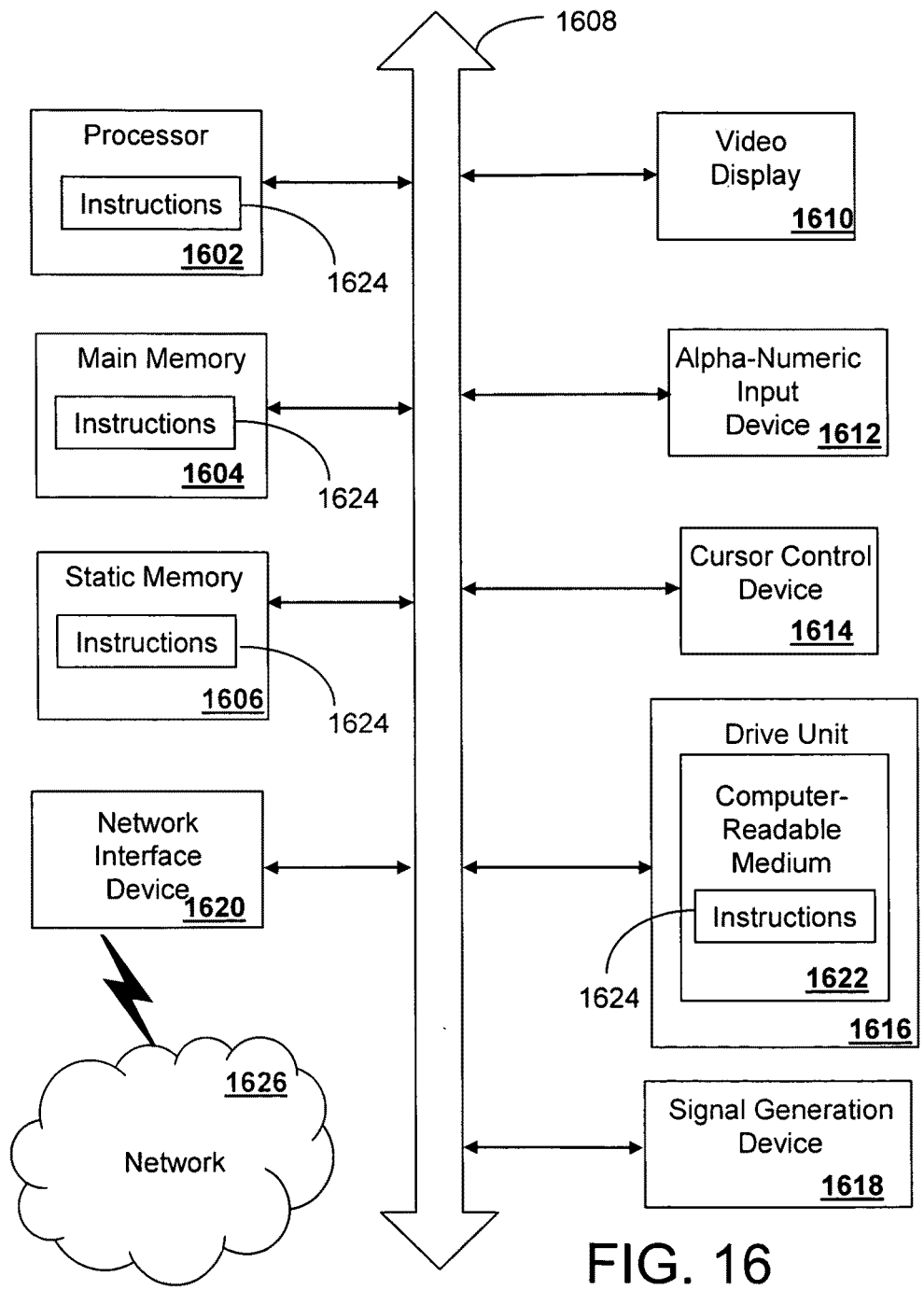
FIG. 16 is a schematic diagram of a computer system for executing a set of instructions that, when executed, can cause the computer system to perform one or more of the methodologies and procedures described herein.

FIG. 16 is a schematic diagram of a computer system 1600 for executing a set of instructions that, when executed, can cause the computer system to perform one or more of the methodologies and procedures described above. In some embodiments, the computer system 1600 operates as a standalone device. In other embodiments, the computer system 1600 can be connected (e.g., using a network) to other computing devices. In a networked deployment, the computer system 1600 can operate in the capacity of a server or a client developer machine in server-client developer network environment, or as a peer machine in a peer-to-peer (or distributed) network environment.

The machine can comprise various types of computing systems and devices, including a server computer, a client user computer, a personal computer (PC), a tablet PC, a laptop computer, a desktop computer, a control system, a network router, switch or bridge, or any other device capable of executing a set of instructions (sequential or otherwise) that specifies actions to be taken by that device. It is to be understood that a device of the present disclosure also includes any electronic device that provides voice, video or data communication. Further, while a single computer is illustrated, the phrase "computer system" shall be understood to include any collection of computing devices that individually or jointly execute a set (or multiple sets) of instructions to perform any one or more of the methodologies discussed herein.

The computer system 1600 can include a processor 1602 (such as a central processing unit (CPU), a graphics processing unit (GPU, or both), a main memory 1604 and a static memory 1606, which communicate with each other via a bus 1608. The computer system 1600 can further include a display unit 1610, such as a video display (e.g., a liquid crystal display or LCD), a flat panel, a solid state display, or a cathode ray tube (CRT)). The computer system 1600 can include an input device 1612 (e.g., a keyboard), a cursor control device 1614 (e.g., a mouse), a disk drive unit 1616, a signal generation device 1618 (e.g., a speaker or remote control) and a network interface device 1620.

The disk drive unit 1616 can include a computer-readable storage medium 1622 on which is stored one or more sets of instructions 1624 (e.g., software code) configured to implement one or more of the methodologies, procedures, or functions described herein. The instructions 1624 can also reside, completely or at least partially, within the main memory 1604, the static memory 1606, and/or within the processor 1602 during execution thereof by the computer system 1600. The main memory 1604 and the processor 1602 also can constitute machine-readable media.

In the various embodiments of the invention, the storage medium can be used to store dataset comprising spatio-temporal data, but can also be used to store derivative data. Derivative data can include, but is not limited to temporal location of segments, statistical variables, class of patterns, matrices of sequential dependency, coordination dynamics modes, source locations and dynamics.

Dedicated hardware implementations including, but not limited to, application-specific integrated circuits, programmable logic arrays, and other hardware devices can likewise be constructed to implement the methods described herein. Applications that can include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the exemplary system is applicable to software, firmware, and hardware implementations.

In accordance with various embodiments of the present disclosure, the methods described herein can be stored as software programs in a computer-readable storage medium and can be configured for running on a computer processor. Furthermore, software implementations can include, but are not limited to, distributed processing, component/object distributed processing, parallel processing, virtual machine processing, which can also be constructed to implement the methods described herein.

The present disclosure contemplates a computer-readable storage medium containing instructions 1624 or that receives and executes instructions 1624 from a propagated signal so that a device connected to a network environment 1626 can send or receive voice and/or video data, and that can communicate over the network 1626 using the instructions 1624. The instructions 1624 can further be transmitted or received over a network 1626 via the network interface device 1620.

While the computer-readable storage medium 1622 is shown in an exemplary embodiment to be a single storage medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure.

The term "computer-readable medium" shall accordingly be taken to include, but not be limited to, solid-state memories such as a memory card or other package that houses one or more read-only (non-volatile) memories, random access memories, or other re-writable (volatile) memories; magneto-optical or optical medium such as a disk or tape; as well as carrier wave signals such as a signal embodying computer instructions in a transmission medium; and/or a digital file attachment to e-mail or other self-contained information archive or set of archives considered to be a distribution medium equivalent to a tangible storage medium. Accordingly, the disclosure is considered to include any one or more of a computer-readable medium or a distribution medium, as listed herein and to include recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same functions are considered equivalents.

The present invention can also be embedded in a computer program product, which comprises all the features enabling the implementation of the methods described herein, and which, when loaded in a computer system, is able to carry out these methods. Computer program or application in the present context means any expression, in any language, code or notation, of a set of instructions intended to cause a system having an information processing capability to perform a particular function either directly or after either or both of the following a) conversion to another language, code or notation; b) reproduction in a different material form.

Applicants present certain theoretical aspects above that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

What is claimed is:

1. A method of analyzing at least one dataset having temporal and spatial content, the method comprising:
    applying a colorimetric mapping to the at least one dataset based on the spatial content to add colorimetric attributes from a colorimetric space to the at least one dataset, wherein the colorimetric mapping uniquely maps spatial coordinates in a physical space comprising the spatial content of the at least one dataset to spatial coordinates in the colorimetric space for selecting the colorimetric attributes;
    segmenting the dataset into one of a plurality of patterns based on a spatio-temporal analysis of the dataset; and
    analyzing characteristics of each of the plurality of patterns,
    wherein the analyzing comprises: registering characteristics of each of the plurality of patterns in the at least one dataset, performing a statistical analysis of said plurality of patterns, classifying the type of dynamics in each of said plurality of patterns based on a taxonomy of patterns, determining a sequential organization of said plurality of patterns, deciphering a mode of coordination dynamics for each of said plurality of patterns, and estimating a source of observed spatio-temporal activity for each of said plurality of patterns based on said deciphering.

2. The method of claim 1, wherein said at least one dataset comprises neurophysiologic data.

3. The method of claim 1, wherein said applying further comprises:
    selecting the colorimetric space to have a spatial content following the spatial content of the at least one dataset.

4. The method of claim 1, wherein said segmenting comprises:
    localizing phase aggregations in said at least one dataset;
    identifying local maxima;
    detecting dynamical transitions based on said identified local maxima; and
    parsing continuous the at least one dataset into patterns according to the detected dynamical transitions.

5. The method of claim 1, wherein said deciphering further comprises:
    creating time-series to model dynamics of at least one among a single sulcal source, a single gyral source, pairs of uncoupled sources, pairs of coupled sources in-phase, pairs of coupled sources anti-phase, pairs of coupled sources at another phase angle, and pairs of sources with meta-stable dynamics;
    applying a forward model to the sequential organization and collecting resulting dynamics at virtual sensors;
    identifying critical signatures for each case of virtual neurophysiologic signals in terms of frequency dynamics, relative phase dynamics, and amplitude dynamics;
    comparing characteristics of each of the plurality of patterns with said critical signatures; and
    inferring an underlying coordination dynamics for each of said plurality of patterns.

6. A system for analyzing spatio-temporal data, the system comprising:
- a storage element for receiving at least one dataset having temporal and spatial content;
- a processing element configured for:
  - applying a colorimetric mapping to the at least one dataset based on the spatial content to add colorimetric attributes from a colorimetric space to the at least one dataset, wherein the colorimetric mapping uniquely maps spatial coordinates in a physical space comprising the spatial content of the at least one dataset to spatial coordinates in the colorimetric space for selecting the colorimetric attributes;
  - segmenting the dataset into one of a plurality of patterns based on a spatio-temporal analysis of the dataset; and
  - analyzing each of the plurality of patterns based on said selected characteristics
- wherein the analyzing comprises: registering characteristics of each of the plurality of patterns in the at least one dataset, performing a statistical analysis of said plurality of patterns, classifying the type of dynamics in each of said plurality of patterns based on a taxonomy of patterns, determining a sequential organization of said plurality of patterns, deciphering a mode of coordination dynamics for each of said plurality of patterns, and estimating a source of observed spatio-temporal activity for each of said plurality of patterns based on said deciphering.

7. The system of claim 6, wherein said at least one dataset comprises neurophysiologic data.

8. The system of claim 6, wherein said processing element is further configured during said applying for:
- selecting the colorimetric space to have a spatial content following the spatial content of the at least one dataset.

9. The system of claim 6, wherein processing element is further configured during said segmenting for:
- localizing phase aggregations in said at least one dataset;
- identifying local maxima;
- detecting dynamical transitions based on said identified local maxima; and
- parsing continuous the at least one dataset into patterns according to the detected dynamical transitions.

10. The system of claim 6, wherein said deciphering further comprises:
- creating time-series to model dynamics of at least one among a single sulcal source, a single gyral source, pairs of uncoupled sources, pairs of coupled sources in-phase, pairs of coupled sources anti-phase, pairs of coupled sources at another phase angle, and pairs of sources with meta-stable dynamics;
- applying a forward model to the sequential organization and collecting resulting dynamics at virtual sensors;
- identifying critical signatures for each case of virtual neurophysiologic signals in terms of frequency dynamics, relative phase dynamics, and amplitude dynamics;
- comparing characteristics of each of the plurality of patterns with said critical signatures; and
- inferring an underlying coordination dynamics for each of said plurality of patterns.

* * * * *